United States Patent [19]
Nathan et al.

[11] Patent Number: 6,057,099
[45] Date of Patent: *May 2, 2000

[54] DETECTION OF NUCLEIC ACID SEQUENCES

[75] Inventors: Asher Nathan, Bet-Shemesh; Yaron Tikochinski, Jerusalem, both of Israel; Ed Rudd, Wolburn, Mass.; Guido Krupp, Kiel, Germany

[73] Assignee: Intelligene Ltd., Jerusalem, Israel

[ * ] Notice: This patent is subject to a terminal disclaimer.

[21] Appl. No.: 08/849,447

[22] PCT Filed: Dec. 1, 1995

[86] PCT No.: PCT/US95/15581

§ 371 Date: Sep. 29, 1997

§ 102(e) Date: Sep. 29, 1997

[87] PCT Pub. No.: WO96/17087

PCT Pub. Date: Jun. 6, 1996

[30] Foreign Application Priority Data

Dec. 2, 1994 [IL] Israel ......................................... 111857

[51] Int. Cl.[7] .................. C12Q 1/68; C12P 19/34
[52] U.S. Cl. ..................... 435/6; 435/91.2; 435/91.21
[58] Field of Search ............................ 435/6, 91.2, 91.21

[56] References Cited

FOREIGN PATENT DOCUMENTS

WO 89/05533  6/1989  WIPO .
WO 89/05631  6/1989  WIPO .

OTHER PUBLICATIONS

Chetverin, Alexander B., et al., "On the Nature of Spontaneous RNA Synthesis by Qβ Replicase", Institute of Protein Research, Academy of Sciences of the USSR, J. Mol. Biol., 222 (1991), pp. 3–9.

Sousa, Rui, et al., "A mutant T7 RNA polymerase as a DNA polymerase", Dept. of Biochemistry, University of Texas Health Science Center at San Antonio, The EMBO Journal, vol. 14, No. 18, 1995, pp. 4609–4621.

Moore, Melissa J., et al., "Site–Specific Modification of Pre–mRNA: The 2'–Hydroxyl Groups at the Splice Sites", Science, vol. 256, May 15, 1992, pp. 992–997.

Leary, Susan L., et al., "DNA–dependent RNA polymerase from bacteriophage T3 transcribes and amplifies an RNA template in vitro", Lifecodes Corporation, NY, Gene, 1081 (1991), pp. 93–96.

Conrad, F., et al., "Novel properties of T7 RNA polymerase: possible applications in the construction of nuclease–resistant antisense RNAs", Inst. Allg. Mikrobiol., Kiel, Germany, p. 125.

Conrad, R., et al., "New Properties of T7 RNA Polymerase Extend the Range of Modification Interference Analyses and Provide a Strategy for the Design of Highly Nuclease–Resistant Ribozymes", Inst. Allg. Mikrobiol., Kiel, Germany, p. 88.

Nath, Kamalendu, et al., "Covalent Attachment of Polyribonucleotides of Polydeoxyribonucleotides Catalyzed by Deoxyribonucleic Acid Ligase", The Journal of Biological Chemistry, vol. 249, No. 12, Jun. 25, 1974, pp. 3680–3688.

Primary Examiner—Lisa B. Arthur
Attorney, Agent, or Firm—Blank Rome Comisky & McCauley LLP

[57] ABSTRACT

A method for detecting the presence of an assayed nucleic acid sequence in a sample is an essentially two stage-procedure. As illustrated, in a first stage the sample is reacted in a manner which gives rise to the production of a triggering oligonucleotide where the sample contains the assayed sequence. In the second stage, the reaction product is incubated under appropriate conditions with an amplification system whereby, in the presence of triggering oligonucleotide, a large amount of a nucleic acid product is obtained. The detection of this product thus indicates the presence of the assayed sequence in the sample.

20 Claims, 16 Drawing Sheets

DETECTION OF NUCLEIC ACID SEQUENCES

This application is a 371 application of PCT/US95/15581, filed Dec. 1, 1995.

FIELD OF THE INVENTION

The present invention concerns a method and kit for the detection of specific nucleic acid sequence in a sample.

BACKGROUND OF THE INVENTION

Detection of the presence of a specific DNA or RNA sequence in a sample is required for a variety of experimental, diagnostic and therapeutic purposes, e.g. detection of a specific mutation in a sample of amniotic fluid, parenterage testing, testing for incorporation of a viral DNA into a cell's genomic DNA, etc. The task of direct detection of a specific DNA or RNA sequence, which is routinely performed by the use of an appropriately labelled probe, is often hindered by the fact that the specific DNA or RNA is present in a sample only in minute amounts.

Examples of methods which enable the amplification of DNA sequences present in a sample in only minute quantities are: LCR (ligase chain reaction), 3SR (self-sustained sequence replication) or PCR (polymerase chain-reaction). In PCR a sample is contacted with a primer DNA complimentary to a 3' end sequence of the specific DNA, a DNA polymerase and with single DNA nucleotides. Following a number of replication cycles, the sample is enriched with the specific assayed DNA. A typical cycle of PCR comprises three distinct stages: a first stage in which the double-stranded DNA is melted to two single strands; a second stage of annealing of the primer to the single-stranded DNA; and a third stage of polymerization where the annealed primers are extended by the DNA polymerase, to produce a double-stranded DNA. The cycle of melting, annealing and DNA synthesis is repeated many times, the products of one cycle serving as templates for the next ad thus, each successive cycle enriches the sample with the specific DNA.

PCR suffers from several shortcomings, the most serious of which being its lack of specificity. The effective hybridization temperature, i.e. the temperature in which the two strands of DNA hybridize, determines the specificity of the reaction. A low effective hybridization temperature results in a higher percentage of non-specific binding. In PCR this temperature, which is defined by the temperature of the annealing stage, is relatively low and this brings about non-specific binding of the probe to the target sequences resulting in amplification of undesired sequences which brings about a relatively high background reading.

This non-specificity also requires an additional and time-consuming detection procedure such as electrophoretic separation of the amplification products on an agarose gel, in order to separate between the various amplification products, and does not enable detection of the presence of the assayed DNA by a mere detection of amplification.

PCR also suffers from a severe problem of contamination which is due to amplification of sequences that did not originate from the test sample being sequences unintentionally introduced to the sample.

Another disadvantage of PCR is that it is a complex procedure. Typically, each of the stages of melting, annealing and polymerization is carried out at a different temperature, e.g. melting at 94° C., annealing at 50° C. and polymerization at 72° C. Since the samples have to be constantly cycled through several temperatures a special apparatus is required rendering the procedure laborious and time consuming.

Another shortcoming of PCR is in the time required therefor. A typical cycle lasts several minutes, and usually 25–30 cycles are required to produce sufficient copies of amplified DNA. Thus, a typical PCR even in a completely automated system lasts at least 2 to 3 hours.

Finally, PCR is basically suited for the detection of DNA sequences. Where detection of RNA sequences is desired, RNA has to be converted first to DNA (by reverse transcription). This conversion to DNA requires additional time, effort and enzymes, and also introduces many errors due to the inherent inaccuracy of reverse transcription.

It should be noted that although PCR is advantageous in obtaining large amounts of a specific DNA, such as for producing large quantities of probes for genetic assays, it is often an "over-kill" where merely the presence of a specific DNA sequence in a sample is to be assayed.

Other such methods such as 3SR (WO PCT 89/05631) and Target Nucleic Acid Amplification/Detection (WO PCT 89/05533) are relatively rapid isothermal processes for DNA detection. However, these methods also suffer from relatively effective low hybridization temperatures which are even lower than those of PCR, typically in the range of 37–41° C. These low temperatures drastically reduce the specificity of the procedure due to non-specific probe-target binding, and in cases of clinical diagnostics, this may result in an intolerable level of misdiagnosis.

Additionally, amplification strategies such as Target Nucleic Acid Amplification/Detection that are based on the amplification properties of a replicase-type enzyme are unreliable due to the possibility of spontaneous RNA amplification in the absence of target (Chetverin-AB, et al.,*J. Mol. Biol.*, 222(1), 3–9 (1991)).

It is the object of the invention to provide a method for the detection of a nucleic acid sequence which is:

(i) reliable and sequence specific due to the minimalization of incorrect target-probe hybridization;

(ii) relatively rapid;

(iii) essentially isothermic eliminating the need for specialized and expensive apparatus;

(iv) relatively simple, not requiring the addition of a large number of different enzymes or nucleotide pools; and (v) amenable to automation by enabling the amplification process itself to be indicative of the presence or absence of the nucleic acid sequence to be assayed.

Further objects of the invention will become clear from the following description.

GLOSSARY

Below are the meanings of some of the terms which will be used in the following description and claims:

Assayed nucleic acid sequence—The DNA or RNA sequence which presence in the sample is to be detected.

First oligonucleotide—a DNA molecule or a molecule which is a DNA/RNA hybrid, i.e., a DNA molecule which comprises also RNA nucleotides, which has a double-stranded, i.e. functional promoter, and a 5' end sequence which is complementary to the 5' end portion of the assayed nucleic acid sequence.

Second oligonucleotide—an oligonucleotide being comprised either of DNA nucleotides (dNTPs), or being comprised of both DNA and RNA nucleotides (dNTPs and rNTPs); the second DNA molecule comprises a single-stranded 3' end sequence which is complementary to the 3' end portion of the assayed nucleic acid sequence and further comprises a sequence which can be transcribed to the triggering oligonucleotide (see below). The 3' end sequence of the second oligonucleotide and the 5' end sequence of the first oligonucleotide may be complementary together to the entire assayed nucleic acid sequence or to only a part thereof, leaving an intermediary portion of the assayed nucleic acid sequence having no complementary counterparts in either first or second oligonucleotides.

Third oligonucleotide—a single-stranded oligonucleotide, being comprised either entirely of dNTPs or both dNTPs and rNTPs; the third oligonucleotide is a single-stranded oligonucleotide which is complementary to the intermediary portion of the assayed nucleic acid sequence, the third oligonucleotide is being used when the first and second oligonucleotides complement only part of the assayed nucleic acid sequence, leaving an intermediary portion in the assayed nucleic acid sequence having no complementary counterparts in either the first or the second oligonucleotides.

Detection system—a system of molecules comprising the first oligonucleotide, the second oligonucleotide, and also the third oligonucleotide when same has to be used. The detection ensemble optionally comprises also a ligase. In the presence of the assayed nucleic acid sequence and transcription reagents, the detection ensemble is activated and the triggering oligonucleotide is produced.

Triggering oligonucleotide—an oligonucleotide being transcribed in the detection ensemble by an RNA polymerase; the triggering RNA is comprised both of dNTPs and rNTPs. The triggering oligonucleotide is produced only after activation of the detection ensemble. The triggering oligonucleotide is then capable of triggering transcription in the amplification ensemble (see below) of a reporter of oligonucleotide (see below).

Reporter oligonucleotide—An RNA oligonucleotide or an hybrid RNA/DNA oligonucleotide (an RNA oligonucleotide with some dNTPs). The reporter oligonucleotide is being produced in the amplification ensemble (see below). The production of the reporter oligonucleotide serves as an indication for the presence of the assayed nucleic acid sequence in the sample.

Reporter template sequence—a nucleic acid sequence serving as a template from which the reporter oligonucleotide is being transcribed.

Transcription reagents—RNA polymerase with dNTPs and rNTPs and the remaining agents required for their incorporation into an elongated oligonucleotide produced by the RNA polymerase.

Transcription system—the ensemble of oligonucleotides, nucleotides and RNA polymerase which brings to transcription of an oligonucleotide transcript.

Amplification system—a system comprising the triggering oligonucleotide, other oligonucleotides and transcription reagents required in order to produce the reporter oligonucleotide.

DNA initiation sequence (DIS)—A DNA sequence present downstream of the promoter and which facilitates or enhances transcription of an oligonucleotide sequence present downstream therefrom, by the RNA polymerase.

GENERAL DESCRIPTION OF THE INVENTION

In accordance with one aspect of the invention there is provided a method for detecting the presence of an assayed nucleic acid sequence in a sample, comprising the steps of:

(a) incubating the sample within a detection system comprising:
  (i) a first oligonucleotide having a double-stranded promoter sequence and a 5' end sequence which is complementary to the 5' end portion of the assayed nucleic acid sequence;
  (ii) a second oligonucleotide having a single-stranded 3' end sequence being complementary to a 3' end portion of the assayed nucleic acid sequence, and further having a sequence which can be transcribed into a triggering oligonucleotide capable of initiating a reaction in a transcription system in which a transcription product is produced; the 3' end sequence of the second oligonucleotide and the 5' end sequence of the first oligonucleotide are either complementary together to the entire assayed nucleic acid sequence or to only part thereof, thus leaving an intermediary portion in the assayed nucleic acid sequence having no complementary counterpart in either the first or the second oligonucleotide, in which case the detection ensemble further comprises
  (iii) a third oligonucleotide being complementary to said intermediate portion;

said first, second and third oligonucleotides, being either DNA oligonucleotides, a DNA oligonucleotide comprising RNA nucleotides (rNTPs), or a DNA oligonucleotide comprising analogs of DNA nucleotides (dNTPs) or of rNTPs;

(b) providing conditions allowing hybridization of said first oligonucleotide and said second oligonucleotide, and where present also said third oligonucleotide, with said assayed nucleic acid sequence, and optionally providing also a ligase to allow ligation of adjacent ends of said first, second and third oligonucleotides;

(c) providing conditions allowing the production of said triggering oligonucleotide, said conditions comprising the provision of:
  (i) an RNA polymerase;
  (ii) 4 species of nucleotides, of which at least two are rNTPs and of the remaining two
    at least one is a non-rNTP being a dNTP or a nucleotide analog other than rNTP or dNTP, or
    at least one is a combination of rNTP and said non-rNTP of the same nucleotide species, the said non-rNTP being in abundance over said rNTP; and
  (iii) conditions allowing the incorporation of rNTPs into the triggering oligonucleotide produced by the RNA polymerase;

(d) contacting the triggering oligonucleotide with an amplification system in which the triggering oligonucleotide induces formation of reporter oligonucleotides; and (e) detecting the presence of said reporter oligonucleotide, positive results indicating the presence of said assayed nucleic acid sequence, in said sample.

In accordance with the present invention there is no need to amplify the assayed DNA sequence, but rather its presence brings about production of large quantities of the reporter oligonucleotide. The method of the invention thus involves production and amplification of an oligonucleotide which is other than the assayed DNA sequence, the latter being the case in PCR.

Another advantage of the method of the invention is that contrary to DNA amplification, several RNA polymerase enzymes can operate on the same template simultaneously thus the overall transcription process is relatively rapid.

The method of the invention thus provides a relatively specific, rapid and uncomplicated method with the detection of an assayed nucleic acid sequence in a sample.

The method of the invention can be carried out in several reaction vessels, e.g. two: one comprising the detection system in which a triggering oligonucleotide is being produced; the other comprising the amplification system in which a reporter oligonucleotide is being produced, upon introduction of the triggering oligonucleotide from the first vessel. It is possible, however, also to perform all the reaction steps simultaneously in a one reaction vessel.

The first or second oligonucleotides are typically DNA oligonucleotides although may at times be of advantage to replace some of the dNTPs with rNTPs. Such a substitution may be at times of advantage in order to increase the affinity between the first and second oligonucleotides and the assayed DNA since RNA-DNA interactions have a higher affinity than DNA-DNA interactions. However, use of first, second and third oligonucleotides which are comprised entirely of dNTPs, is generally preferred in accordance with the invention.

Said first oligonucleotide may comprise a double-stranded and hence functional promoter. Alternatively, the promoter is a priori single-stranded in at least an essential part thereof and a sequence complementary to the single-stranded portion of the promoter is added during or after step (b). Namely, it should be understood that by the above definition of first oligonucleotide, the functional promoter may be present a priori or may be assembled in situ during the performance of the assay in the assay vessel.

Steps (a) and (b) of the method of the invention may be modified to increase the specificity of the detection and/or prevent production of short sequences of transcription products from the first oligonucleotide, which may increase the background signal. These modifications include, for example, an additional step after step (b) of raising the temperature to a point where only perfectly matched hybrids of assayed nucleic acid sequences and first and second oligonucleotides (and also third oligonucleotide if present) remain hybridized while all other hybrids in which the individual strands do not perfectly match one another are melted. The reformation of mismatched hybrids after melting can be prevented by the addition of blocker molecules which compete with the assayed nucleic acid sequence by hybridizing at a high affinity to the first or to the second oligonucleotide. Such a modification ensures that the triggering oligonucleotide is produced only in case of a perfect match between the assayed nucleic acid sequence and the first and second oligonucleotides.

in order to avoid production of undesired short transcripts from the first oligonucleotide which would have an effect of increasing assay "noise", it is possible to assemble the promoter of the first oligonucleotide in stages. In this case, the first oligonucleotide comprises a promoter which is single-stranded in at least an essential part thereof and thus non-functional. After the formation of hybrids of the assayed nucleic acid sequence and the first and second oligonucleotide, blocker oligonucleotides, which may be DNA, RNA, DNA/RNA hybrids, etc. are added which hybridize only to the free first oligonucleotide in such a manner so as to avoid subsequent hybridization thereof of the missing promoter part and cannot hybridize to first oligonucleotides present in the hybrid. An oligonucleotide comprising the missing promoter part is then added, which completes only the promoter of first oligonucleotide in said hybrid rendering it functional and thus enabling the production of the triggering oligonucleotide. In contrast to this, the molecule comprising the missing promoter is unable to hybridize with free first oligonucleotides which are blocked, and thus no short transcripts are produced from the free first oligonucleotides.

Free first oligonucleotides can also be separated from hybrids of assayed nucleotides and first and second oligonucleotides, for example, by having the second oligonucleotides bound to a solid support, e.g., magnetic beads and thus, after hybridization, removing all non-bound, i.e. free, oligonucleotides.

In principle, the triggering oligonucleotide transcribed in the detection system (steps (a)–(c)) could be an RNA oligonucleotide. However, it was found in accordance with the invention, that the amplification achieved at the next method steps wherein the transcript is DNA is limited and it was surprisingly found that incorporation of dNTPs or other nucleotides other than rNTPs, into the triggering oligonucleotide, works to advantage in dramatically increasing the rate of amplification in the amplification system.

While the following explanation should not be construed as limiting, it is believed that the increase in the rate of amplification results from the lower affinity of DNA-RNA hybridization than RNA-RNA hybridization. In the amplification system, the triggering oligonucleotide serves as a template for an RNA polymerase. After formation of one oligonucleotide by the RNA polymerase, in order for an RNA polymerase to use the triggering RNA as a template once more, the transcribed oligonucleotide should be detached from the template. Where both the template and the transcribed oligonucleotides are both RNA, the very high affinity which exists between two RNA strands, avoids such detachment; against this, where the triggering oligonucleotide comprises dNTPs, and particularly where the transcription in the amplification system is performed under conditions whereby dNTPs are occasionally incorporated in the extending oligonucleotide, the affinity of hybridization between the two oligonucleotides is much lower and accordingly the transcription product detaches itself from the template and a new oligonucleotide can then be transcribed.

The incorporation of dNTPs into the extending triggering oligonucleotides, is also advantageous in that the so formed oligonucleotide is more resistant to degradation by RNAase, which may be present in the sample.

RNA polymerase, such as T7 polymerase (T7 Pol), can, under appropriate conditions, incorporate nucleotides other than rNTPs into an extending RNA oligonucleotide. Such conditions include mixtures of magnesium and manganese (F. Conrad, et al., *Bio Eng. Sondernummer* 3, Abstract P 125, 1994; F. Conrad, et al., Abstract in the Second Symposium on Gene Therapy, Apr. 8–9, 1994; F. Conrad, et al., Abstract in RNA Processing Meeting of the RNA Society, May 24–29, 1994). Such conditions may, for example, be the addition into the medium of $Mn^{+2}$, e.g. 2.5 mM, or a combination of $Mn^{+2}$ and $Mg^{+2}$, e.g. 2.5 mM of each ion. For a total modification of the RNA, the transcription system may include, for example, three species of rNTPs and one of dNTP, e.g. rATP, rGTP, rUTP and dCTP. For a partial modification, the rNTP may be added in combination with the corresponding dNTP, and in view of the higher tendency to incorporate rNTP, only some of the incorporated nucleotides will be dNTPs.

In addition to dNTPs, also other types of non-rNTP nucleotides can be used, such as, for example, 190-C, 190-G and others.

In accordance with the present invention, it is also possible to use a mutant T7 RNA polymerase which is capable of utilizing dNTPs and which is capable of synthesizing RNA, DNA or mixed transcripts having both dNTPs and rNTPs (Sousa et al., *EMBO,* 14(18):4609–4621 (1995)).

The present invention also provides by another of its aspects, a kit for carrying out the method of the invention. The kit typically comprises the various oligonucleotides, reagent systems, etc. required for carrying it out. The kit may also comprise one or more viles or other suitable vessels, for carrying out the method. Where the method is carried out in two discreet stages, one of detection, i.e., steps (a)–(c), and the other of amplification, i.e. stages (d)–(e), the kit may include at least two vessels for the performance of this method. Where the method is performed in one stage, i.e. also stages in tendem in one vessel, the kit may comprise at least one vessel, for carrying it. Obviously, the kits may also comprise a plurality of vessels for the performance of several of such assays. Typically, the vessels may already comprise all the necessary reagents and oligonucleotides.

The invention will now be illustrated with reference to some non-limiting specific embodiments described in the following with occasional reference to the annexed drawings.

Figure 1:
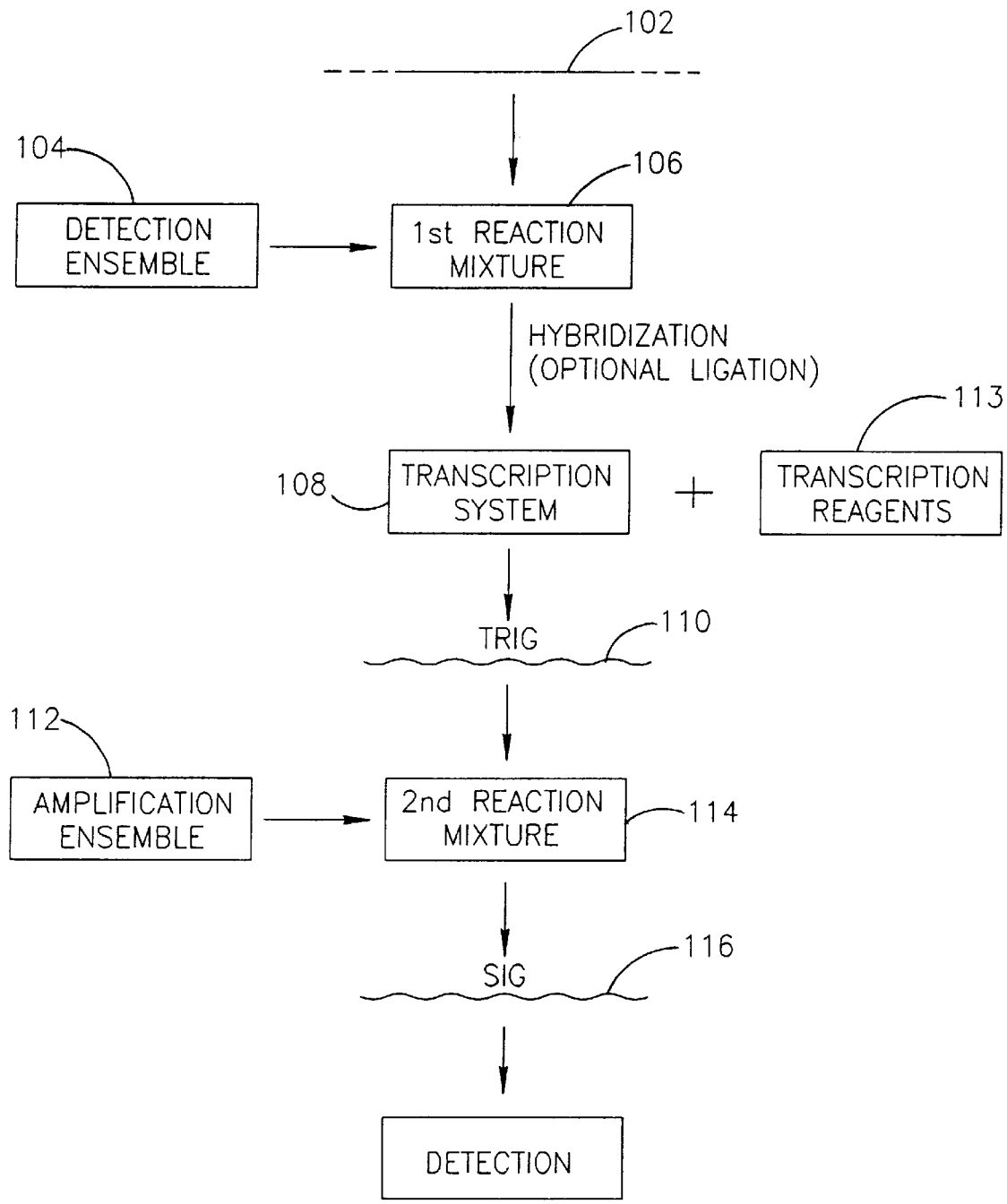
FIG. 1 shows a flow chart of the method of the invention.

In the drawings, various symbols are used which in the context of the present description have the following meanings:

| | |
|---|---|
| Straight line (___) | DNA strand |
| Wavy line (∿∿∿) | An oligonucleotide transcibed from a DNA or another oligonucleotide template |
| A,B,C, etc. . . . | sequences in DNA |
| A',B',C', etc. . . . | sequences in DNA which are complementary to A,B,C, etc., respectively |
| a',b'c', etc. | sequences in an oligonucletoide transcribed from DNA sequences A,B,C, etc. . . . |
| a,b,c, etc. . . . | sequences in a transcribed oligonucleotide complementary to a',b',c', etc. . . . |
| A",B" | sequences in DNA which are partially complementary to DNA sequences A and B |
| TRIG | triggering DNA sequence |
| trig | triggering RNA sequence |
| SIG | signal DNA sequence |
| sig | signal RNA sequence |
| $P^+$ | functional promoter in DNA |
| $P^-$ | non-functional promoter in DNA |
| $p^+$ | functional promoter in a transcribed oligonucleotide |
| $p^-$ | non-functional promoter in a transcribed oligonucleotide |
| A-α,B-β,A'-α',B'-β',C-γ etc. . . . | complementary sequences on the same strand of nucleic acid sequence |
| DIS | DNA initiation sequence |

DETAILED DESCRIPTION OF THE INVENTION

In the figures, the various components are designed by three or four digit numerals. The first digit in a case of a three digit numeral and the first two digits in the case of a four digit numeral represent the figure number and the last two digits represent the component number. In all figures like components have the same component number. Thus, for example, a component 102 in FIG. 1 has the same function as 202 in FIG. 2, etc.

Reference is first made to FIG. 1 showing an overview of the method of the present invention. Nucleic acid sequence 102 which is in this example a DNA sequence, forming part of a genome of an organism in an assayed sample, is contacted with a detection system 104, comprising various DNA oligonucleotides or hybrid DNA/RNA oligonucleotides, the former being preferred [is this correct?] to form a first reaction mixture 106. The reaction mixture is subjected to conditions allowing hybridization of the assayed sequence 102 with corresponding sequences of the oligonucleotides of the of the detection system (see further below).

Following hybridization and optional ligation steps, a transcription system 108 is obtained comprising in accordance with the preferred embodiment, a DNA heteroduplex having a double-stranded, i.e. functional promoter and a downstream DNA sequence which can be transcribed into a transcript 110 which is referred to herein as the triggering oligonucleotide. In order to obtain the triggering oligonucleotide 110, transcription reagents 113 comprising RNA polymerase, rNTPs and dNTPs are added to the transcription system 108. Under appropriate conditions an oligonucleotide, being an RNA oligonucleotide with some incorporated dNTPs will be obtained.

The triggering oligonucleotide is then combined with an amplification system 112 to yield a second reaction mixture 114. The amplification system comprises reagents which in the presence of the triggering oligonucleotide will give rise to the production of large quantities of a transcript 116, referred to herein as the signal oligonucleotide. The detection of the presence of the signal oligonucleltide can then be carried out by any number of means known per se.

Figure 7:
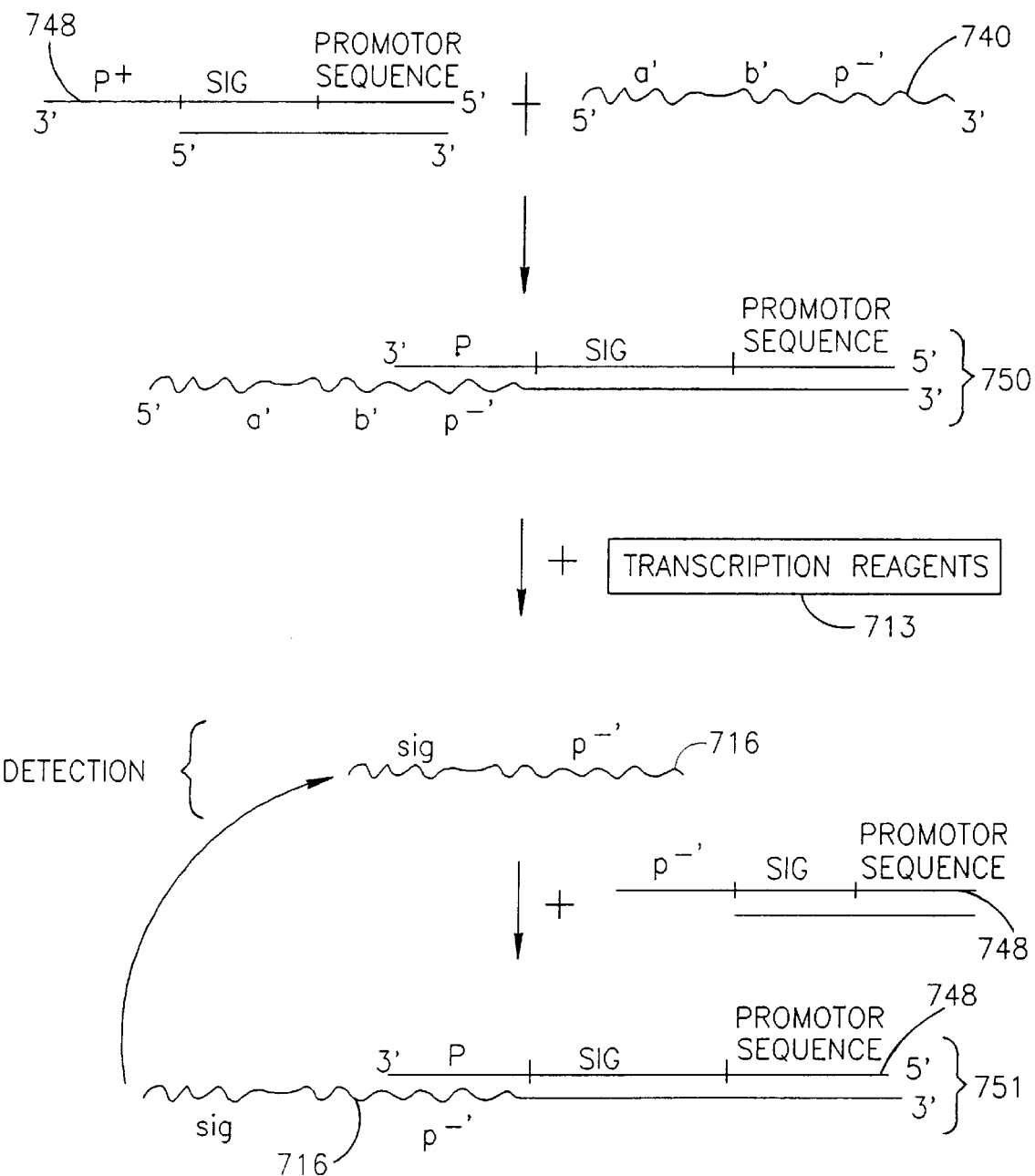
FIGS. 7–8 are schematic representations of embodiments of the amplification system.
Figure 8:
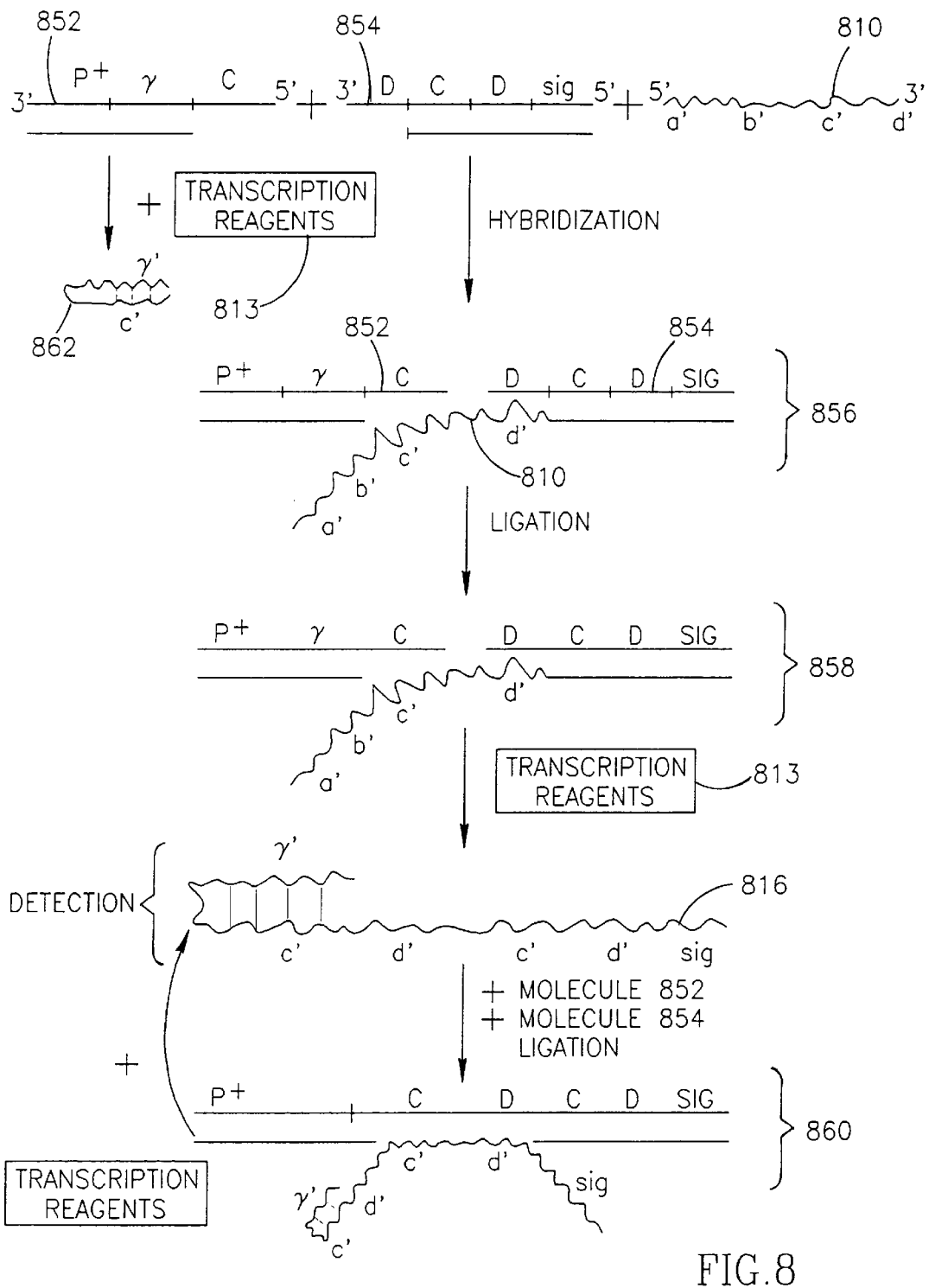

In the following, various features of the invention will be illustrated with reference to some specific embodiments. FIGS. 3–6 describe various embodiments and modifications of the detection system shown in FIG. 2. FIGS. 7–8 show various embodiments of the amplification system and the production of the signal oligonucleotide. FIGS. 9–12 show embodiments of the invention including both the detection and amplification systems.

In the following described embodiments, the first, second and third oligonucleotides are DNA molecules, it being understood that the invention applies *mutatis mutandis,* also to cases where first, second and third oligonucleotides are DNA-RNA hybrids.

Figure 2:
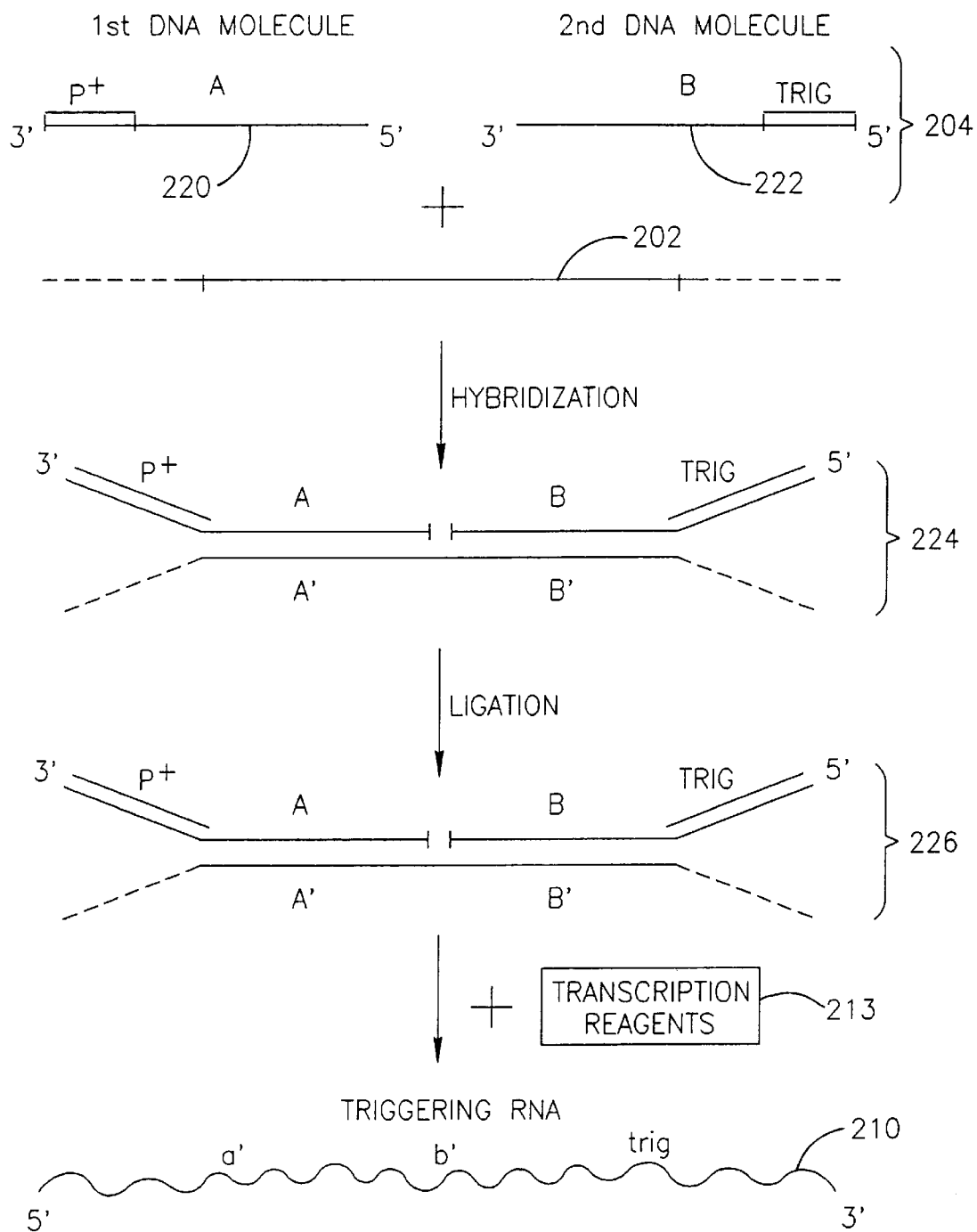
FIG. 2 is a schematic representation of the basic components of the detection system.

Reference is first made to FIG. 2 showing the basic features of the first step in the performance of the method of the invention in which the triggering oligonucleotide is produced. From here on the invention will be described with reference to embodiments in which the assayed nucleic acid sequence is a DNA sequence and it is to be understood that the method is applicable also to the assaying of the presence of RNA sequences, *mutatis mutandis.*

The detection system 204 comprises a first DNA molecule 220 and a second DNA molecule 222. The first DNA molecule 220 comprises a functional, double-stranded promoter $P^+$. The first DNA molecule 220 has a single-stranded sequence A and the second DNA molecule has a single-stranded sequence B linked to a triggering sequence TRIG which may be single or double-stranded. The sequences A and B are complementary to sequences A' and B', respectively, in the assayed DNA 202.

If the assayed DNA 202 is present in the sample, and appropriate conditions for hybridization are provided, a hybrid 224 is produced. In this hybrid the 3' end of sequence B and the 5' end of sequence A are adjacent to one another and are optionally ligated to yield ligation product 226.

Transcription reagents 213 comprise an RNA polymerase such as the T7 polymerase, and a combination of rNTPs and dNTPs as well as a proper combination of manganese and/or magnesium ions to allow incorporation of dNTPs in the transcribed oligonucleotides. As a result, a triggering oligonucleotide 210 having a triggering sequence trig linked to sequences b' and a' is produced.

Figure 3:
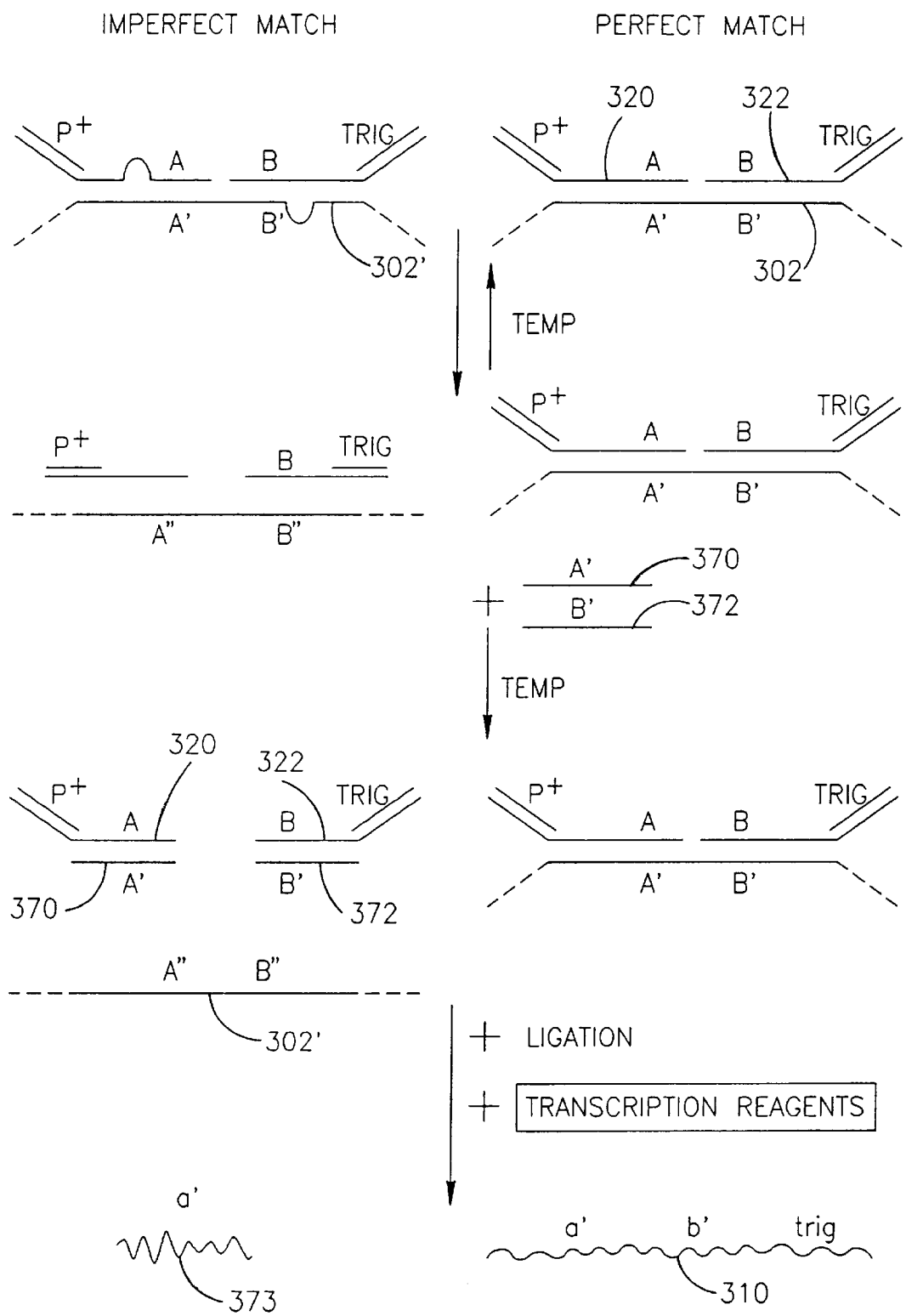
FIGS. 3–6 are schematic representations of embodiments of the detection system.

Reference is now made to FIG. 3 showing a modification of the method outlined in FIG. 2 intended to eliminate almost entirely the possibility of obtaining a positive result in case of an imperfect match between the oligonucleotides of the detection system and the assayed DNA. The right-hand side of FIG. 3 shows the case of a perfect match between the first 320 and second 322 DNA molecules and the assayed DNA 302; and the left-hand side of the figure shows the case of an imperfect match, where the assayed DNA 302' comprises sequences A" and B" (the mismatch being represented schematically by loops in sequence A and sequence B").

After hybridization between the DNA sequences, as described in connection with FIG. 2, the temperature is raised to a temperature wherein there will be a total melting of the hybridized DNA sequences in case of an imperfect match and less than total melting, e.g. 50%, in case of a perfect match. This temperature depends, as known, on a number of factors including the length of the DNA sequences as well as the relative proportion of the nucleotide bases A and T versus G and C, and has to be determined empirically in each case.

At this temperature, short DNA fragments (or other short oligonucleotides) 370 and 372 having sequences A' and B', respectively, are added which hybridize to the single-stranded A and B sequences. The temperature is then lowered and a ligase and transcription reagents are then added if not a priori present. In the case of an imperfect match, only small RNA transcripts 373 with the sequence a' will be produced whereas in the case of a perfect match, a transcript 310 having the triggering sequence—trig will be produced.

In case there is a significant difference between melting temperatures of the above two hybrids, for example, where the hybrid in the case of any imperfect match between the first DNA molecule and the assayed DNA has a melting temperature $T_1$ which is higher than melting temperature $T_2$ of the hybrid containing the second DNA molecule, the method may proceed as follows: addition of first DNA molecule 320 and second DNA molecule 322; addition of blocker molecule 370; raising temperature to $T_1$; lowering temperature to $T_2$; addition of blocker molecule 372; lowering temperature to reaction temperature; addition of transcription reagents 313.

In order to ensure that the blocker molecules 370 and 372 have an advantage over the mismatched assayed DNA in re-hybridization with the first and second DNA molecule when the temperature is lowered, these blocker molecules should be in excess to the assayed DNA. In addition, it is possible to add an extra arbitrary sequence to first molecule 320 and to add a sequence complementary to said extra sequence, to blocker molecule 370. This extra sequence raises the affinity between the blocker molecule and the first DNA molecule to be higher than the affinity between the first DNA molecule and the mismatched portion of the assayed DNA. An extra arbitrary sequence can be added in a similar manner, to second DNA molecule and blocker molecule 372 respectively.

Figure 4:
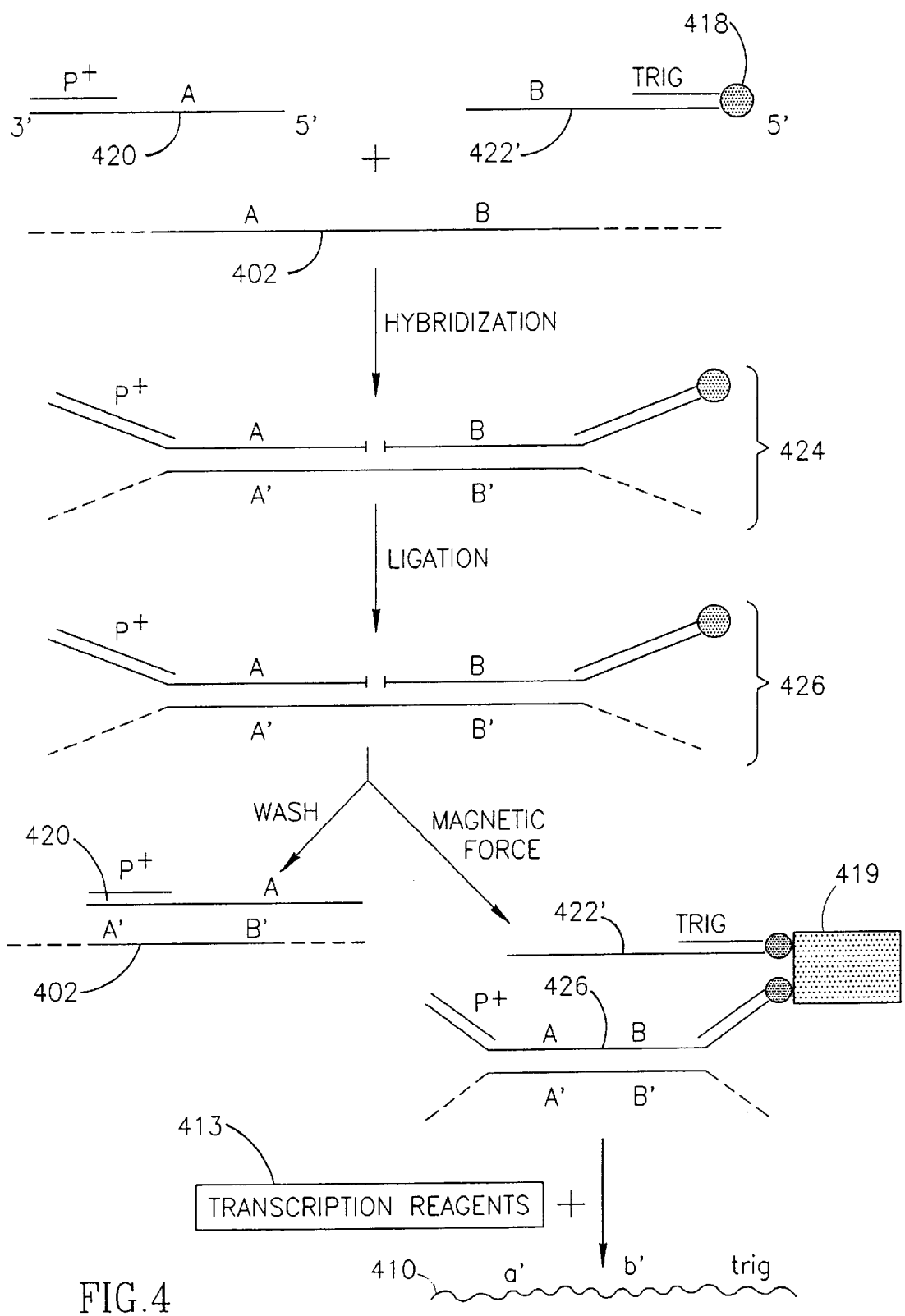

Reference is now made to FIG. 4 showing a modification in the method outlined in FIGS. 2 and 3 which eliminates the production of short RNA transcript having the sequence a', which are transcribed from the first DNA molecule. First molecule 420 is identical to first molecule 220 in FIG. 2. Second molecule 422' is essentially identical to second molecule 222 in FIG. 2 and is linked to a magnetic bead 418 at its 5' terminal. Assayed DNA 402 is added to produce hybrid 424 optionally followed by ligating to yield ligation product 426. Magnetic force is then applied. All molecules linked to a magnetic bead, namely, free second DNA molecules 422 and ligation product 426 as well as hybrids 424 in case there is no ligation), are drawn to the magnet 419, while molecules unlinked to magnetic beads, namely, first DNA molecules 420 and assay DNA molecules 402 are washed away. Transcription reagents 413 are added to the test vessel, if not a priori present and since the only DNA molecules containing a promoter in the reaction mixture are ligation product 426, the only transcripts which are produced are the triggering oligonucleotide 410 containing the trig sequence. This modification enables detection of the presence of assayed DNA by the detection of mere amplification of oligonucleotides with no need to determine which type of oligonucleotide has been produced.

Figure 5:
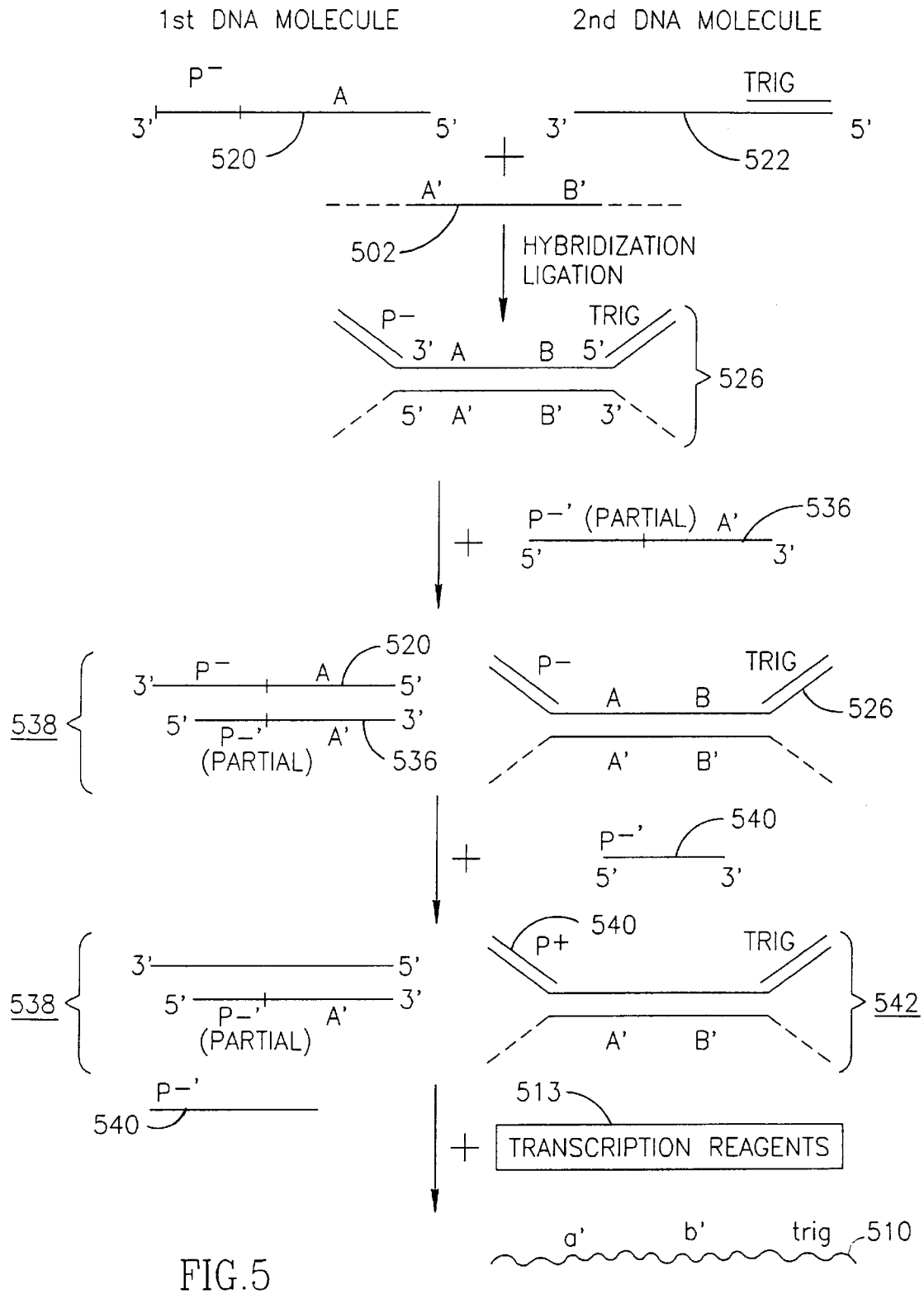

Reference is now made to FIG. 5 which shows another modification in the method outlined in FIGS. 2 and 3 also intended to eliminate production of contaminating short transcripts having sequence a' transcribed from first DNA molecules. First DNA molecule 520 contains only a single-stranded non-functional promoter ($P^-$). Assayed DNA 502 is added and allowed to hybridize with first 520 and second 522 DNA molecules and after addition of a ligase, ligation product 526 is obtained. To the reaction mixture a blocker molecule 536 is added containing at its 5' end a sequence which is partially complementary to part of the promoter sequence ($P^{-'}$ partial)) linked to a sequence A' complementary to sequence A or to a part thereof. The blocker molecule 536 can hybridize only with free first DNA molecules 520 to yield hybrid 538 and cannot bind to hybrid 526 since in this hybrid sequence A is already double-stranded. Since $P^{-'}$ is only partially complementary to the promoter, the presence of mismatches in hybrid 538 makes its promoter non-functional. At this stage, DNA molecules 540 containing a sequence $P^{-'}$ complementary to the full single-stranded promoter of the first DNA molecules are added. Molecules 540 can hybridize with hybrids 526 to give a hybridization product 542 having a functional double-stranded promoter. However, molecules 540 cannot hybridize with blocked hybrid 538, since the promoter of the hybrid is already partially double-stranded. By this modification free first molecules are blocked from forming a functional double-stranded promoter so that when transcription reagents 513 are added to the reaction mixture, no short transcripts are produced and only triggering oligonucleotides 510 are formed. The method outlined in this figure can be used in combination with the method of FIG. 2 in which case blocker molecule 540 contains also sequence A" of FIG. 2 and is used to increase the specificity of the method.

Figure 6:
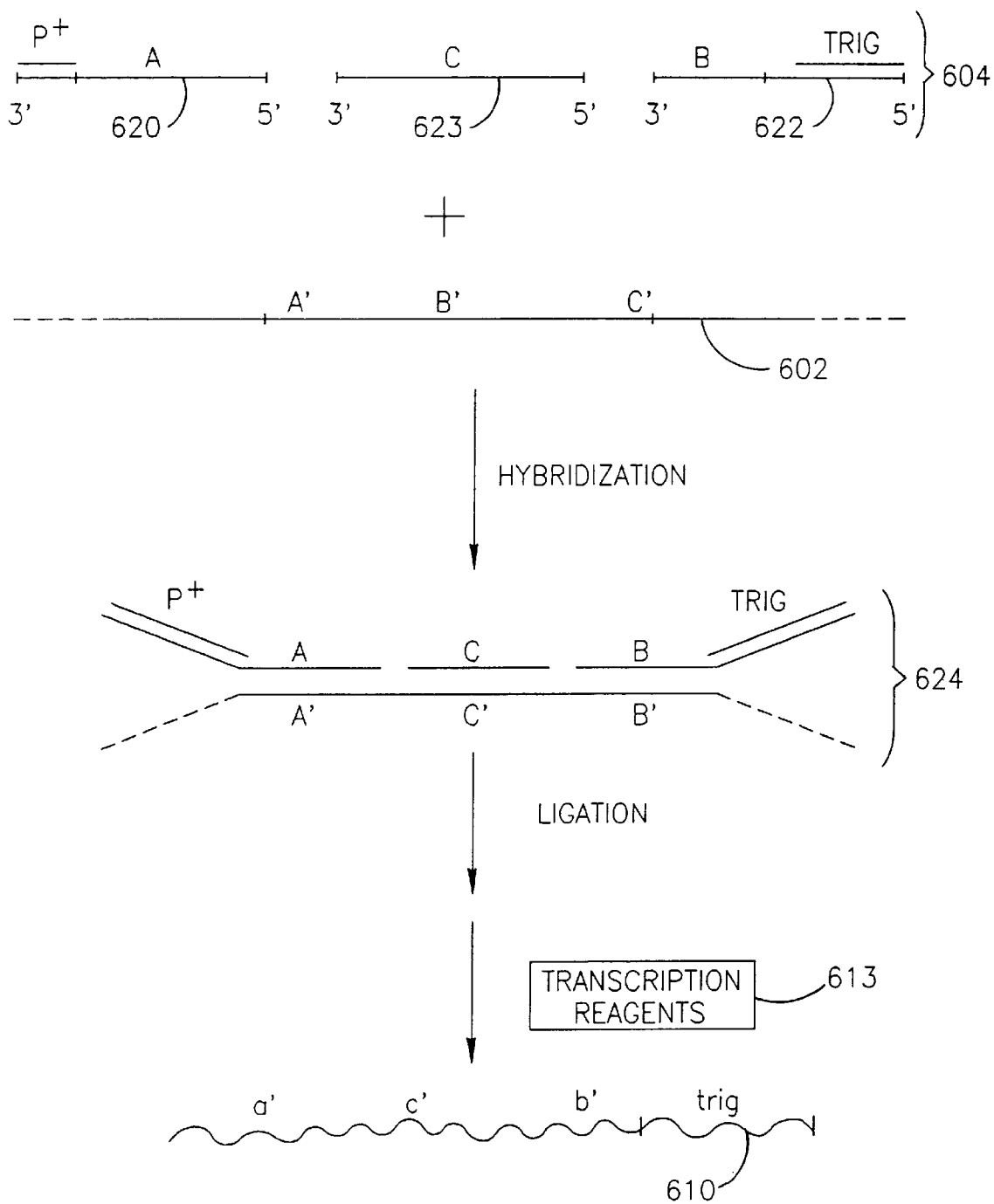

Reference is now made to FIG. 6 showing a modification of the embodiment depicted in FIG. 2. In accordance with this embodiment, detection system 604 comprises a first DNA molecule 620, a second DNA molecule 622 and a third DNA molecule 623. These three molecules comprise single-stranded sequences A, B, C which are complementary to corresponding sequences A', B', C' in the assayed DNA sequence 602. Following hybridization, a hybridization product 624 is produced which is formed from the first, second and third DNA molecules on the one hand and the assayed DNA sequence on the other hand. Following an optional step of ligation and a step of addition of transcription reagents 613 (if not a priori present), a triggering oligonucleotide 610 is produced in a manner similar to that described in FIG. 1.

Reference is now made to FIG. 7 showing an amplification system according to an embodiment of the invention. According to this embodiment, the triggering oligonucleotide 710 product of the detection ensemble, contains sequences a' and b' linked to the triggering sequence $p^{-\prime}$ which is a single-stranded sequence complementary to an essential part of the single-stranded promoter $P^-$ of a fourth DNA molecule 748. Fourth DNA molecule 748 contains at the 3' end of its template strand a single-stranded promoter sequence $P^{-\prime}$, linked to a double-stranded signal DNA sequence SIG, which is in turn linked to a DNA sequence capable of being transcribed to the triggering sequence p–' termed "promoter-sequence" in the figure. In some cases $P^-$ of molecule 748 may be partially double-stranded and is only single-stranded in a part essential for the promoter's function. When oligonucleotide 710 is added to molecule 748, the triggering sequence $p^{-\prime}$ of molecule 710 hybridizes with sequence $P^-$ of molecule 748 to form a heteroduplex 750 having a double-stranded functional promoter $P^+$. Upon addition of transcription reagents 713, transcript 716, which is the signal oligonucleotide comprising the signal sequence "sig" and sequence $p^{-\prime}$, is produced. Transcript 716 can in turn hybridize with the fourth DNA molecules 748 to produce heteroduplexes 751 which in the presence of the transcription reagents 713 bring to production of more transcripts 716 in a self-amplifying manner. Thus, the amounts of signal oligonucleotides in the medium increases rapidly and in a short period of time large quantities are produced. The signal molecule can then be detected by means known per se, either by detecting of the presence of the specific signal sequence or by merely determining the quantity of the oligonucleotides in the reaction medium, by means known per se, for example, by change in light absorbance. The presence of the signal oligonucleotide indicates the existence of the assayed DNA in the original sample.

Reference is now being made to FIG. 8 which shows an amplification system according to another embodiment of the invention. The triggering oligonucleotide 810, product of the detection system, comprises sequences a' and b' linked to sequences c' and d' which are complementary to the single-stranded sequences C and D in the fifth 852 and sixth 854 DNA molecules, respectively. Fifth DNA molecule 852 comprises a double-stranded functional promoter $P^+$ linked to a double-stranded sequence γ linked to a single-stranded sequence C. Sequence γ and sequence C are complementary to each other. Sixth DNA molecule 854 comprises at the 3' end of the template strand a single-stranded sequence D, linked to double-stranded sequences, C, D and a signal DNA sequence.

The two DNA molecules 852 and 854 are allowed to hybridize with transcript 810 to yield a heteroduplex 856. In this hybridization product molecules 852 and 854 are joined together by RNA transcript 810. A ligase is added to ligate the adjacent ends of DNA molecules 852 and 854 to yield a ligation product 858. In the presence of transcription reagents 1213, an oligonucleotide 816 is produced. In this molecule sequence γ' and c' which are complementary, form a loop. The signal sequence sig in molecule 816 can then be detected by means known per se. In addition, oligonucleotide 816 can be further made to hybridize with more fifth 852 and sixth 854 DNA molecules to form a heteroduplex 860 optionally followed by ligation. In the presence of the transcription reagents 813 more transcripts 816 are transcribed from hybrid 860 which in turn cause formation of more heteroduplexes 860, and the reaction can continue in a self-amplifying manner.

In the presence of a transcription system 813, fifth DNA molecules 852, which comprises a functional promoter brings to the production of short transcripts 862. These short transcripts, however, cannot interfere with the hybridization of the fifth DNA molecules 852 with the triggering oligonucleotide 810 or with transcript 816, wince due to the presence of complementary sequences c' and γ' a loop is formed.

Figure 9:
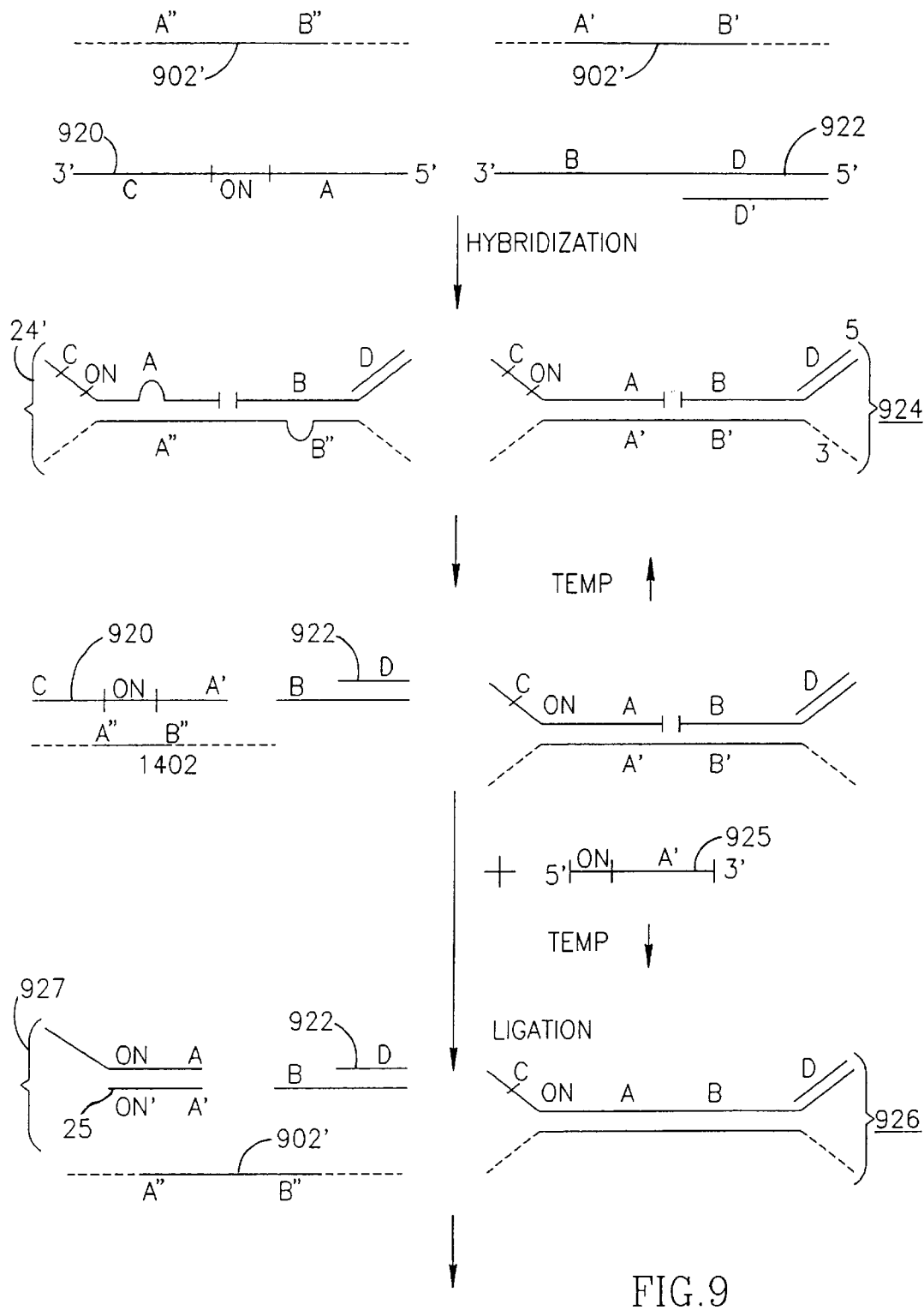
FIGS. 9–12 show embodiments of manners of carrying out the invention, including both the detection system and the amplification system, according to further embodiments of the invention.
Figure 9A:
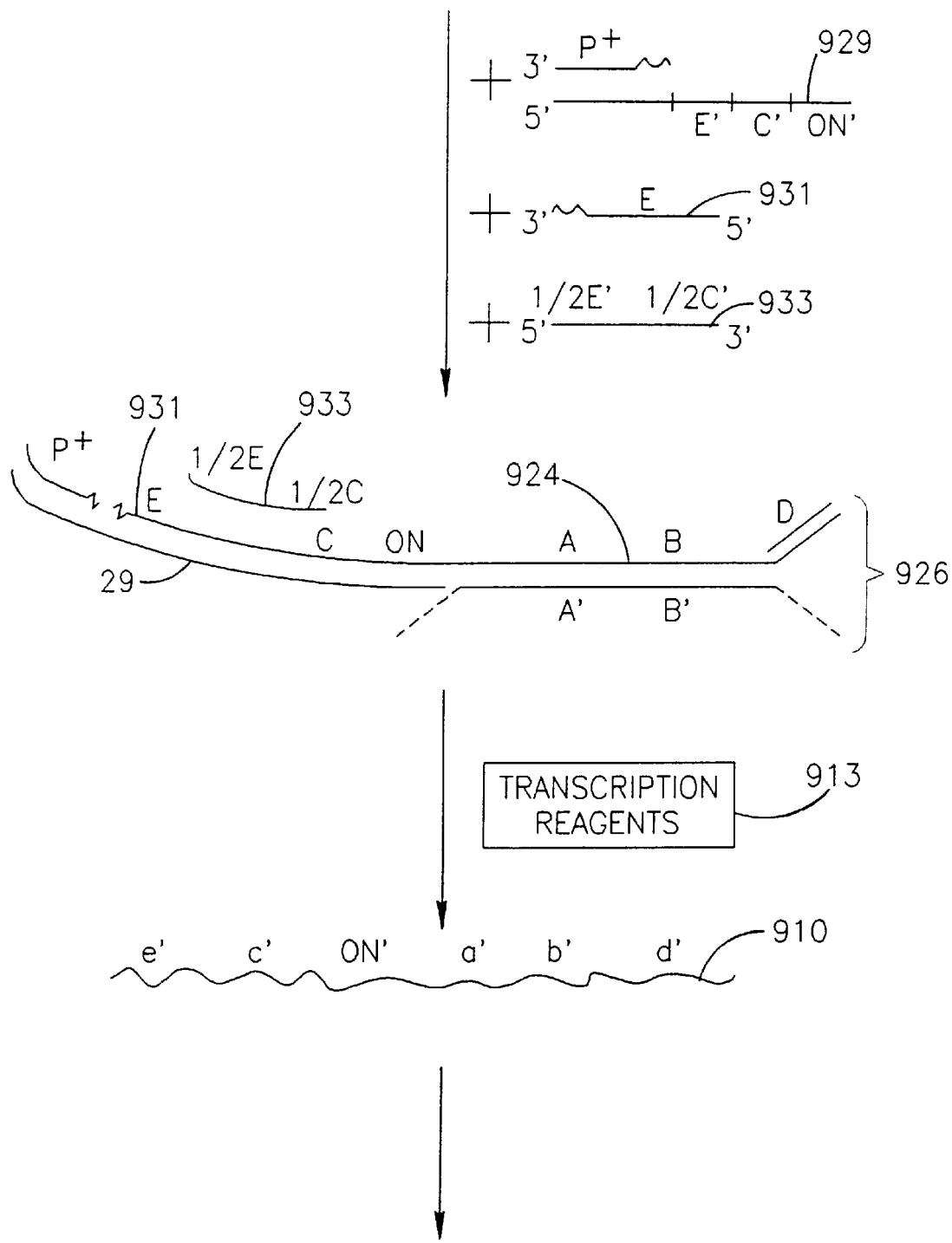
Figure 9B:
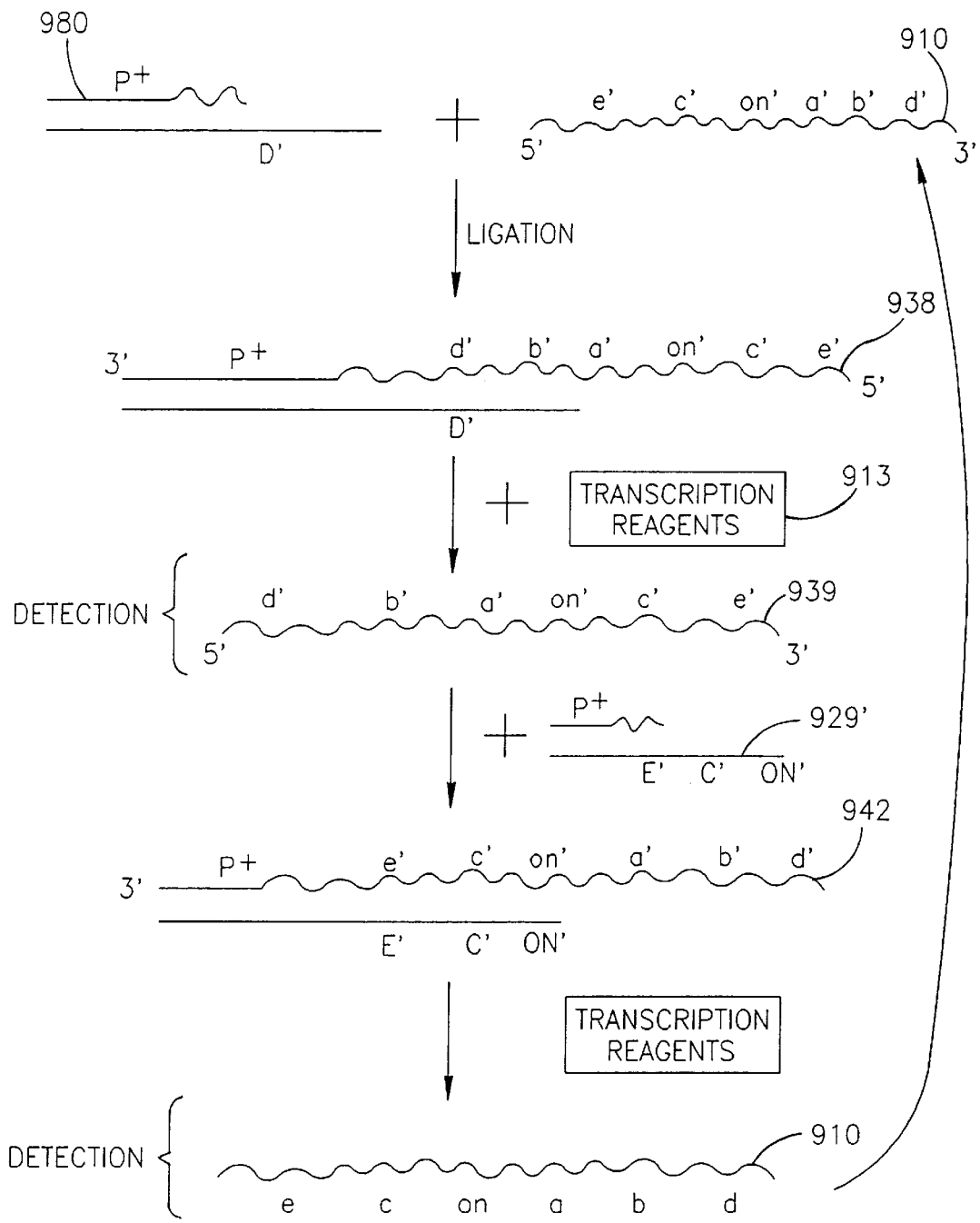

Another embodiment of the invention is shown in FIG. 9. First DNA molecule 920, which in this embodiment is completely single-stranded, comprises at its 3' end an arbitrary sequence C, linked to a short sequence of 1 to 5 bases termed ON and linked to a sequence A. Second DNA molecule 922 comprises at its 3' end a sequence B linked to an arbitrary double-stranded sequence D–D'.

Sequence A of the first molecule is complementary to sequence A' in the 5' end portion of the assayed DNA and sequence B of the second DNA molecule is complementary to the sequence B' in the remaining 3' end portion of the assayed DNA 902.

At times the sample contains also a sequence 902' comprising sequences A" and B" which are not fully complementary to sequences A and B in first and second molecules 920 and 922, respectively. This may be so, for example, in the case of genetic polymorphism. The molecules in the mixture are allowed to hybridize, producing perfect hybridization products 924 and imperfect hybridization products 924'.

In a similar manner as in the embodiment described in FIG. 3, conditions are provided so that essentially only imperfect hybrids 924' are melted. A blocker molecule 925 is added to the mixture which during cooling hybridizes to free first DNA molecules 920. The free first DNA molecules include both first DNA molecules present a priori in the sample and first DNA molecules which were freed from hybrid 924' after melting. Molecule 925 comprises sequences ON' and A' complementary to sequence ON and A, respectively, in molecule 920 and consequently hybrid 927 is produced. In order to ensure that all free DNA molecules will be blocked by blocker molecules 925, an excess of the blocker molecules is added.

To the sample are now added molecule 929, 931 and 933 which together are able to form a functional promoter with the ligation product 926 of hybrid 924, while they are not able to form a functional promoter with hybrid 927, thus avoiding the production of short transcripts having the sequence c-on-a.

Molecule 929, termed herein "promoter molecule", comprises a double-stranded promoter $P^+$. One or a few of the nucleotides at the 5' end of the template strand of the promoter are optionally RNA nucleotides. The non-template strand of the promoter is linked to sequence E', C' and ON'.

Molecule 931 termed herein "adapter molecule" comprises a single-stranded DNA sequence optionally having one or a few RNA nucleotides at its 3' end. The purpose of the adapter molecule is to provide a standard sequence having an initial RNA nucleotide which can bind to the RNA nucleotide of the promoter at its one end and to the first DNA molecule (with the aid of a joiner molecule) on its other end, in a case where an RNA molecule is required on the 3' end. When an RNA molecule is not required, the adapter molecule provides a standard sequence common to all reactions. Alternatively, the sequence contained in the adapter molecule may be added to each first DNA molecule when synthesized so that the need for a separate molecule is eliminated.

Molecule 933 termed herein "joiner molecule", it comprises at its 5' end a part (e.g. a half) of E' and at its 3' end a part (e.g. a half) of C'. This molecule serves to join adapter molecule 931 and first DNA molecule 920. In addition, hybridization with this molecule renders the ON sequence essential for hybridization of the promoter molecule 929 to first DNA molecule 920. The fact that the ON sequence becomes essential avoids binding of promoter molecule 929 to blocked hybrid 927 in which the ON sequence is covered, and thus the production of short contaminating sequences is avoided.

When the molecules are added to hybrid 924, joiner molecule 933 joins the 3' end of molecule 920 (in the C sequence) and the 5' end of adapter molecule 931 (in the E sequence). After this joining, the promoter molecule 929 can hybridize to sequence E of the adapter molecule 931 and sequences C and ON in first molecule 920. A ligase then ligates the adjacent ends of the RNA nucleotides both in promoter molecules 929 and adapter molecule 931 (when present) resulting in hybrid 935. Adjacent RNA nucleotides can be ligated by the $T_4$ DNA which is known to be able to ligate between RNA Nucleotides (Moore et al., *Science*, 256, 992–997, (1992). Ligation that occurs when the 3' molecule is comprised of RNA and the 5' molecule is comprises of DNA and also efficiently ligated by $T_4$ DNA ligate (Nath and Hurwitz, *J. Biol. Chem.*, 249, 3680–3688 (1974).

Promoter molecules 929, together with the remaining components cannot bind to blocked hybrid 927 since in this hybrid the sequence ON is blocked, which blockage prevents hybridization.

In the presence of transcription system 913, transcript 910 is produced.

The amplification system comprises promoter molecule 929', being the same as molecule 929 and an opposite promoter molecule 980 that is a promoter which is a double-stranded promoter linked to a sequence D', complementary to sequence d' in the transcript 910. Transcript 910 hybridizes to D' sequence of opposite promoter 980 and with the aid of a ligase a hybrid 938 is formed. In the presence of a transcription system 913, a new transcript 939 is transcribed. The template of this transcript is the RNA sequence of hybrid molecule 938. It is known that RNA can serve as a transcript for RNA production (Leary S. L. et al., *Gene*, 106, 93–6 (1991). Transcript 939 can hybridize with promoter molecule 929' to yield hybrid 942. The product of hybrid 942 is again molecule 910 which can activate opposite promoter 980 and so on. In this embodiment the transcription product of each hybrid 938 or 942 activates the reciprocal promoter in a "ping pong" manner.

RNA polymerase which is an essential feature of the detection system has a tendency to add another rNTP at the end of the extending RNA oligonucleotide which is usually identical to that which preceded it. This so called "n+1" nucleotide can then interfere with the ligation stage between the promoter and the template triggering oligonucleotide.

However, it was found in accordance with the invention that where an incomplete promoter is used as part of the amplification system and the triggering oligonucleotide serves both in order to complete the promoter sequence and to provide a template sequence in the amplification stage, the "n+1" phenomena does not interfere with the transcription process. In other words, where the extra nucleotide is within the promoter, there is no interference or very little interference with normal transcription. Thus, in the embodiment shown in FIGS. 10–12, use is made, in the amplification system, with such an incomplete promoter.

Figure 10:
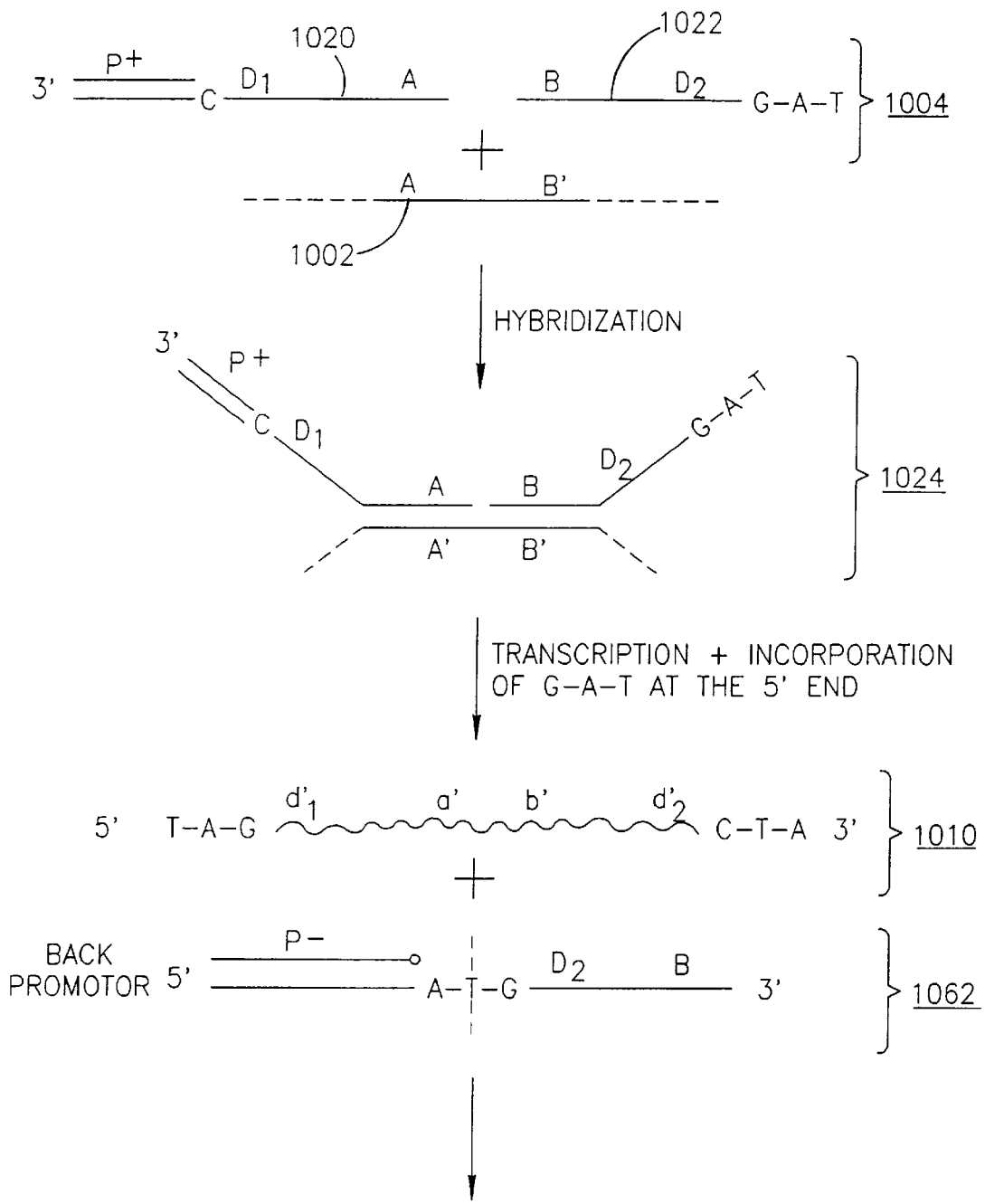
Figure 10A:
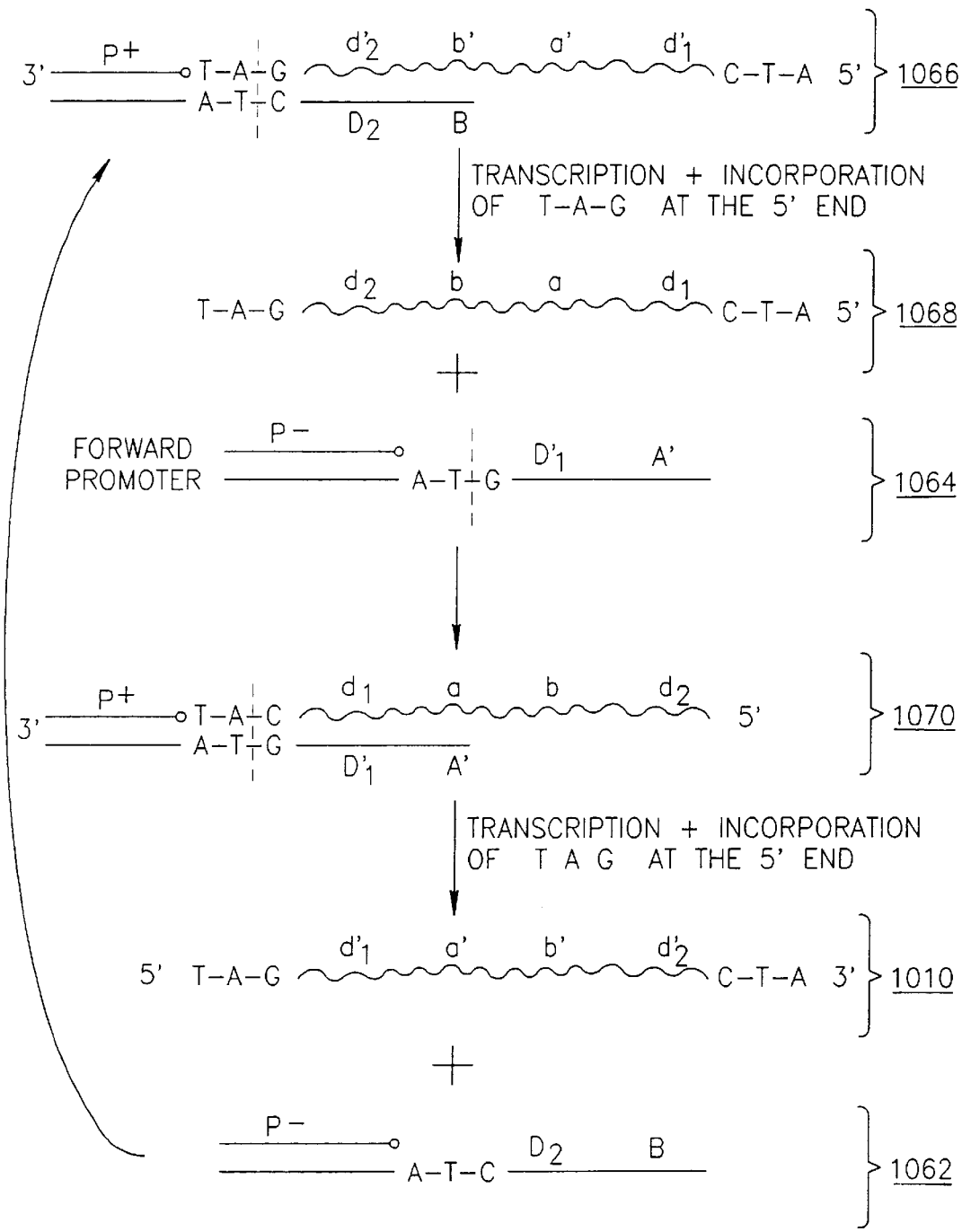

The detection system 1004 of the embodiment shown in FIG. 10 comprises a first DNA molecule 1020 and a second DNA molecule 1022. The first DNA molecule 1020 has a functional promoter $P^+$ followed by a single-stranded coding DNA with sequences $D_1$ and A. The second DNA molecule 1022 is single-stranded and comprises sequences B and $D_2$. The first nucleotide in $D_1$ is c and the last three nucleotides in $D_2$ are GAT and their significance will be elaborated further below. Sequences A and B are complementary to sequence A' and B' in the assayed DNA 1002. When the DNA molecules of the detection system 1004 are combined with a sample comprising the assayed DNA sequence 1002, which may for example be a genomic DNA, and conditions are provided for hybridization, a hybrid 1024 is produced. The hybridization stage may be followed by ligation, by including a ligase in the detection system, whereby the adjacent ends of sequences A and B are joined together.

In the presence of an RNA polymerase, such as the T7-pol, and the provisions of appropriate conditions for the incorporation of both DNA and RNA nucleotides, as explained below, a triggering oligonucleotide 1010 is being produced having the sequences $d_1'$, a', b' and $d_2'$, $d_2'$ ending with the triplet CTA (which are complementary to the GAT in the second DNA molecule). The nucleotide at the 3' end of the D1 sequence in the first DNA molecule was in this specific example a C and accordingly, the nucleotide G would be incorporated in the 5' end of the triggering oligonucleotide 1010. However, in the presence of the triplet GAT, a priori appearing in the system, in abundance over the nucleotide G, e.g. in a ratio of 10:1, there will typically be an incorporation of this triplet at the 5' end of the transcribed oligonucleotide 1010.

The amplification system of this embodiment comprises two promoters, one is a back promoter 1062 and the other is a forward promoter 1064. Both promoters are not fully functional as they lack two nucleotides in the 5' end of the template strand, which in this specific case are the nucleotides T and A, complementary to the nucleotides A and T, respectively, in the non-template strand. The back promoter 1062 comprises the sequences $D_2$ and B which are complementary to the sequences $d_2'$ and b' of the triggering oligonucleotide 1010. Upon hybridization of triggering oligonucleotide 1010 with the back promoter 1062, a hybrid 1066 is produced wherein the incorporated A and T nucleotides complement the promoter and thus a functional promoter is obtained. In the presence of the ligase, there will be a ligation between the adjacent ends of the promoter and the triggering oligonucleotides, although it was found that it is not essential for initiation by transcription of the promoter and it is functional even without ligation. Furthermore, should there be for any reason an n+1 nucleotide, i.e., an extra nucleotide after the nucleotide T, this will not interfere with initiation of transcription by the promoter, as was found in accordance with the invention and also pointed out above.

Following transcription and in cooperation of a TAG triplet in a similar manner to that described above, a transcript 1068 is produced which has the sequence $d_2$, b, a and $d_1$ with the triplet TAG at the 5' end and the triplet CTA at the 3' end. The hybridization of transcript 1068 with back promoter 1064 perform hybrid 1070 and then transcription and incorporation of a TAG at the 5' end of the transcript is performed in a similar manner as that described above and there results a transcript which is in fact identical to the triggering oligonucleotide and therefore was indicated with the same numeral, 1010. This transcript can then combine with the backward promoter 1064 and the reaction thus proceeds in a self-amplifying "ping-pong" manner.

In accordance with the present invention it was found that where an RNA oligonucleotide is used as a template, there is a need for a DIS. It was found that a DIS of two dNTPs usually suffices although routinely the DIS should be in the range of 2–20 nucleotides. This is in fact the function of the sequences $D_1$ and $D_2$ in the first and second DNA molecule. Sequence $D_2$ may for example comprise 1–3 G nucleotides at its 5' end preceding the triplet GAT. In this case, the medium will comprise dCTP instead of rCTP and accordingly deoxy C nucleotides will be incorporated into oligonucleotides 1010 and thus the 3' end of this nucleotide will comprise several consecutive dNTPs (in this case deoxy C nucleotides). This chain of dNTPs at the end of sequence of $d_2'$ will then serve as the DIS in hybrid 1066. Against this, $D_1$ sequence in the first DNA molecule 1020 will comprises several consecutive C nucleotides and accordingly in the 3' end of the $D_1$ sequence in transcript 1068 there will be a small chain of dNTPs which will thus serve as the DIS in hybrid 1070.

The entire process of the embodiment shown in FIG. 10 can be a two-stage process, i.e., one stage of detection which will proceed until the production of triggering oligonucleotide 1010 and the other stage of amplification. However, one of the big advantages of this embodiment is the fact that the entire process can be performed in one reaction vessel using only one enzyme, the RNA polymerase such as T7-Pol.

Figure 11:
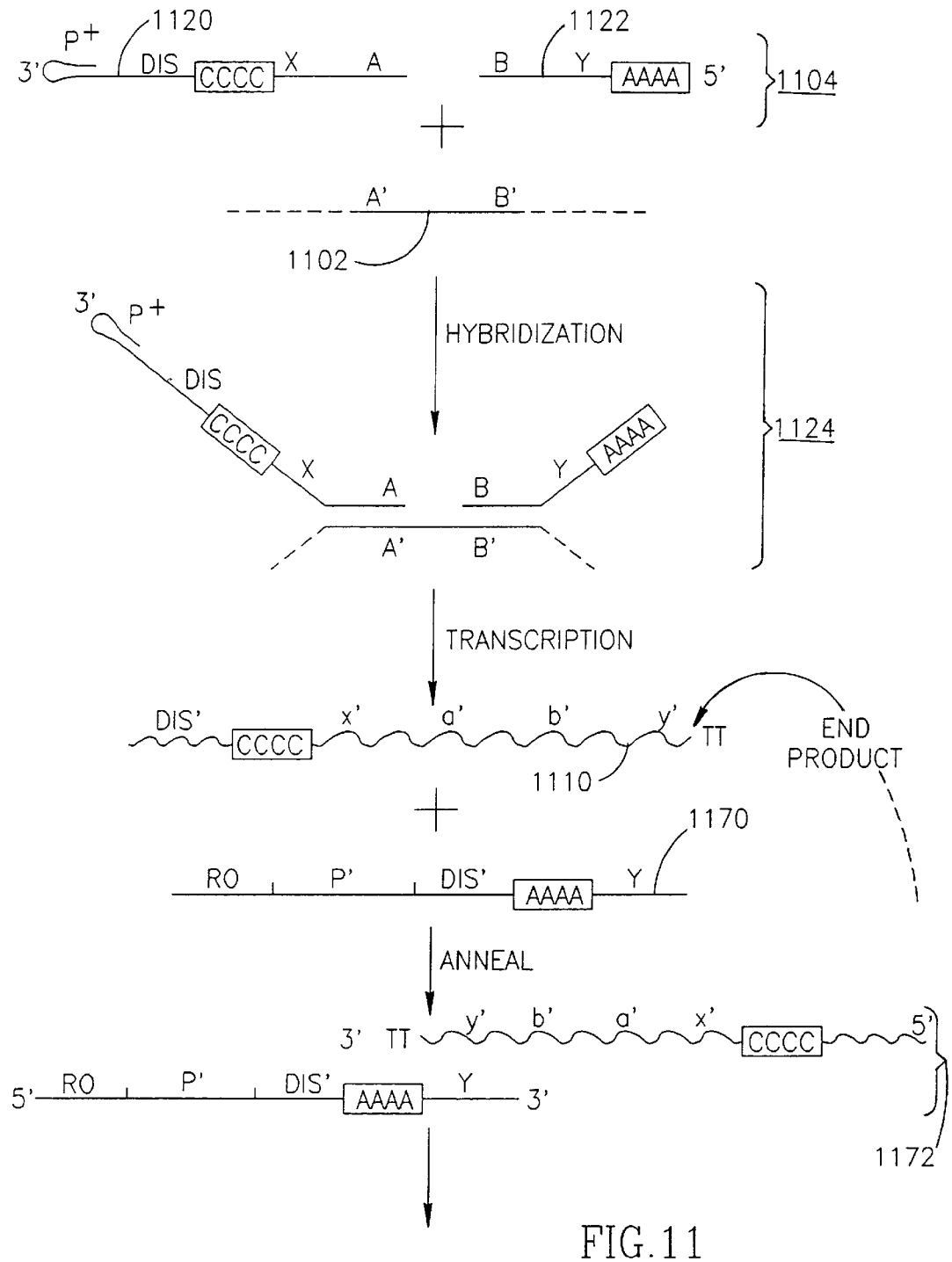
Figure 11A:
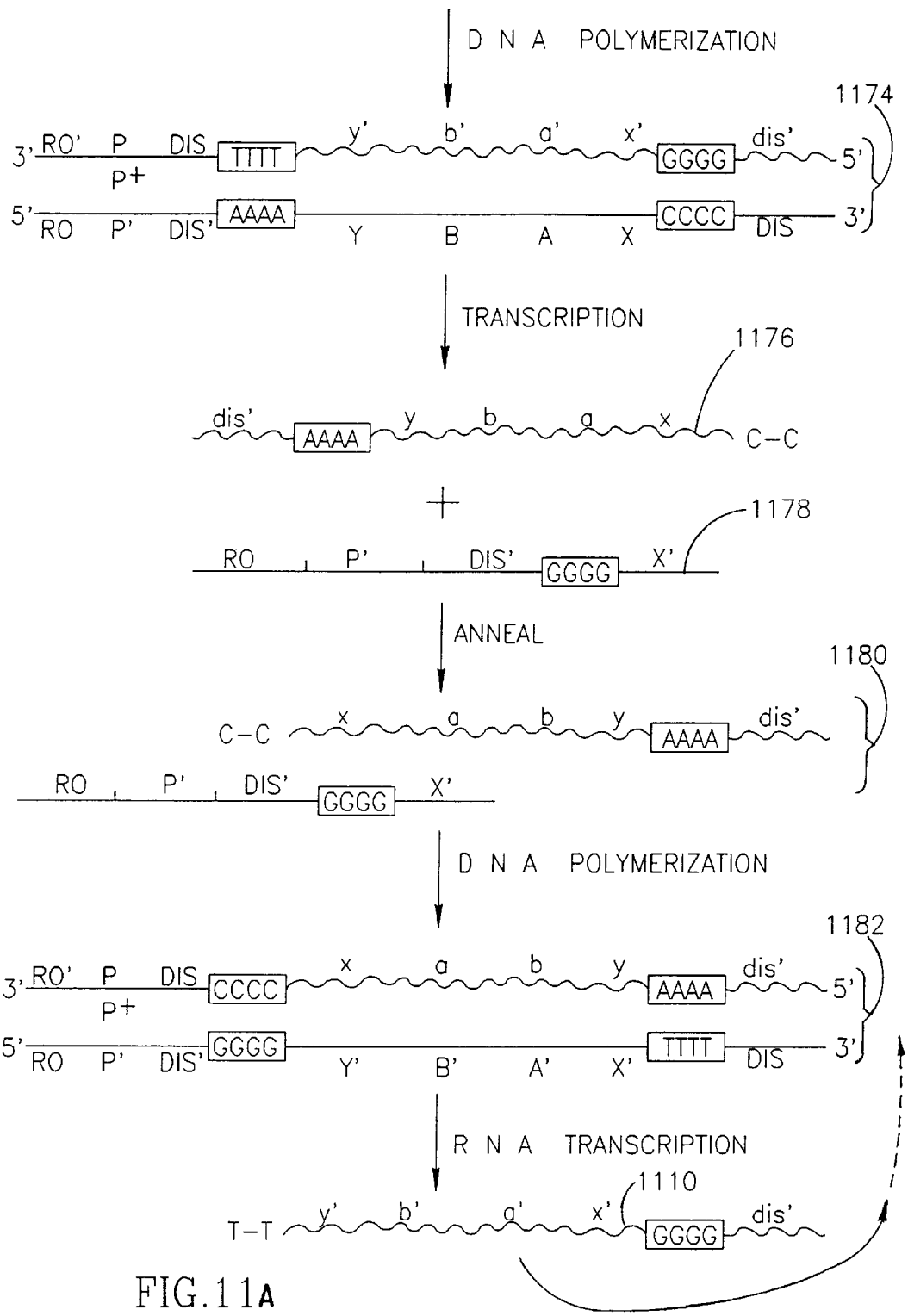

Reference is now being made to FIG. 11 showing a further embodiment of the invention. While this embodiment can be carried out in two stages, a detection stage and then an amplification stage, similarly as in the embodiment shown in FIG. 10, it is preferably carried out in one stage, i.e., the detection and amplification proceedings simultaneously.

The assay system in accordance with this embodiment comprises detection system probes consisting of first a DNA 1120 and a second DNA 1122; four dNTPs; two non-complementary rNTPs, and the specifically shown embodiment is being rGTB and rTTP; an RNA polymerase such as the T7-Pol; DNA polymerase such as the Klenow fragment (this being the Pol-1 DNA polymerase devoid of further proof reading portion or reverse transcriptase; oligonucleotides of the amplification system these being oligonucleotide 1170, referred to herein at times as the "backward oligonucleotide", and oligonucleotide 1178, referred to herein at times as the "forward oligonucleotide"; buffers; and at times also blocker oligonucleotides having a similar function to blocker oligonucleotides described in connection with previous embodiments.

The present embodiment makes use of the property of RNA polymerase which is unable to incorporate stretches of identical dNTPs. In the drawings such stretches of four or more identical dNTPs are shown by way of a rectangle with the letters signifying the respective nucleotide repeated four times therein. Such stretches signify four or more such identical nucleotides.

First DNA molecule 1120 comprises a functional promoter $P^+$ formed as a result of folding of a terminal segment of the DNA molecule. The promoter $P^+$ is followed by a DIS which is then preceded by a stretch of deoxy C nucleotide. This stretch is then followed by a sequence X which is complementary to a sequence in the forward oligonucleotide 1178 (see below) which is in turn followed by the sequence A complementary to sequence A' which is the first part of the assayed DNA sequence 1102. Second DNA molecule 1122 comprises the sequence B which is complementary to the sequence B' in the assayed DNA sequence 1102 followed by a sequence Y which is the same as the sequence Y in the backward oligonucleotide 1170. These two sequences are then followed by stretch of deoxy A nucleotide. The 3' end should preferably be modified, e.g. by dideoxy NTPs, to prevent the DNA polymerase from from extending the 3' end and doubling back on itself.

After mixing with the assayed DNA and providing conditions allowing hybridization, a hybrid 1124 is formed and in the presence of an RNA polymerase a transcript is produced which is a triggering oligonucleotide 1110. Triggering oligonucleotides comprises rG, rT, dA and dC nucleotide. In view of the inability of the RNA polymerase to transcribe the multi-A stretch at the 5' end of the second DNA molecule, only part of this sequence is transcribed.

Triggering oligonucleotides 1110 comprises sequence Y' which is complementary to sequence Y in the backward oligonucleotide 1170 and upon provision of the appropriate condition, the two oligonucleotides anneal to form hybrid 1172. Oligonucleotide 1170 comprises a readout system RO, a non-template promoter sequence P' followed by DIS and a stretch of A nucleotide. In the presence of the DNA polymerase, DNA stretches complementary to the single strands of hybrid 1170 are produced and a double-stranded oligonucleotide 1174 is thus produced. This double-stranded oligonucleotide comprises a functional promoter $P^+$ and consequently, in view of the presence of the RNA polymerase, the oligonucleotide 1176 is transcribed. Here again, in view of the inability of the RNA polymerase to transcribe stretches of identical DNA nucleotide, the multi-G sequence is only partially transcribed. Transcript 1176 comprises a sequence X which is complementary to the sequence X' in forward oligonucleotide 1178 and the two can then anneal to form hybrid 1180 and following DNA polymerization similarly as above a double-stranded oligonucleotide 1182 is formed. Upon transcription the RNA transcript which is produced is in fact identical to the triggering oligonucleotide 1110 which can thus again anneal with forward oligonucleotide 1170 to repeat the entire process.

The RO sequences are readout sequences and under appropriate conditions they can be made to incorporate labelled nucleotide and thus the presence of labelled DNA will indicate the presence of the assayed nucleic acid sequence 1102 in the sample. Thirdly, the readout system may also be based on the quantity of oligonucleotides produced in the system.

By a modification of the embodiment of FIG. 11, rather than having an a priori DIS sequence, such a sequence may be introduced during transcription in a similar manner as in the embodiment of FIG. 10.

In view of the fact that the transcription always ends within a stretch of identical nucleotide, the property of an RNA polymerase to incorporate an "n+1" oligonucleotide will have little effect on the system since usually the "n+1" nucleotide is identical to the preceding nucleotide.

Figure 12:
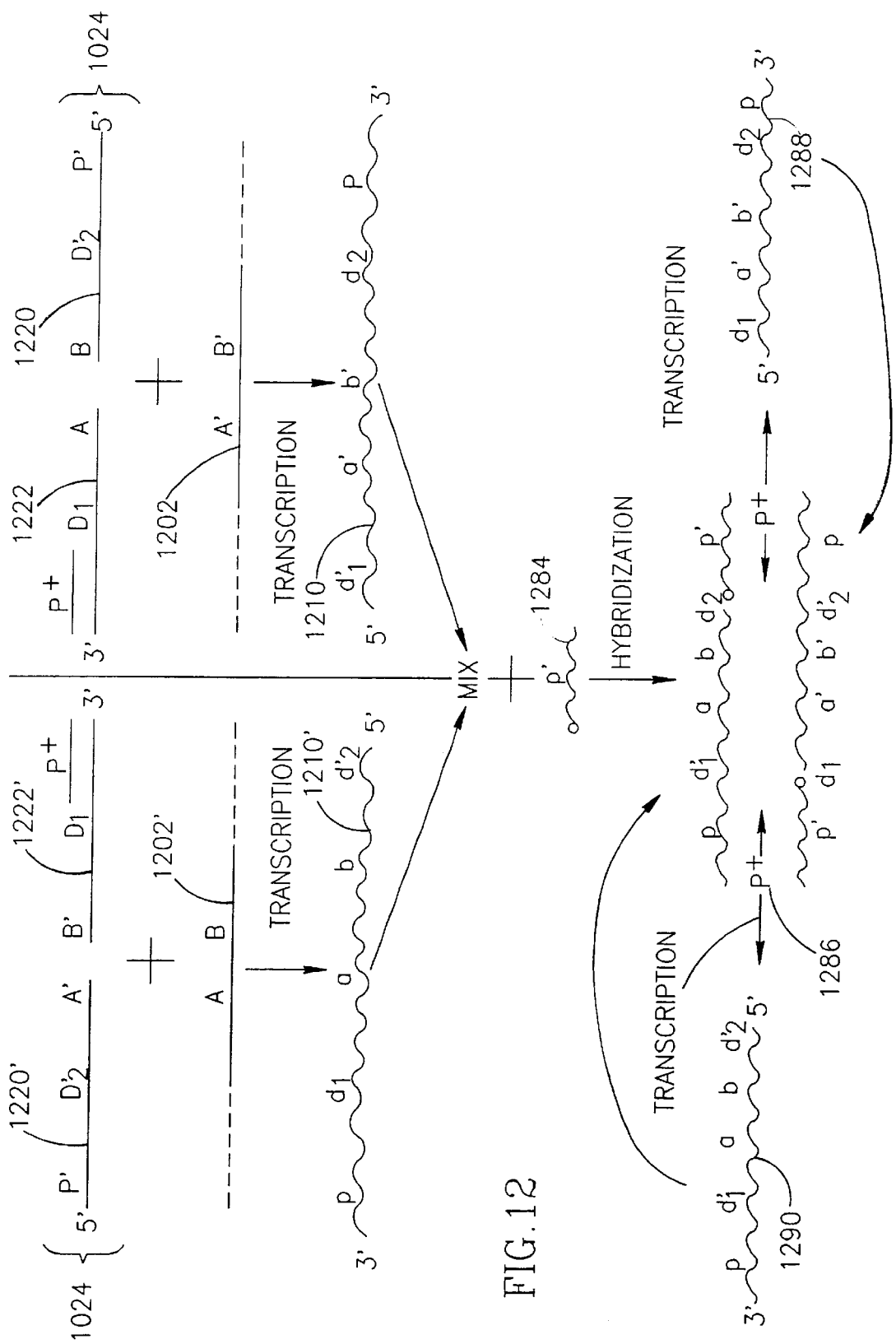

Reference is now being made to FIG. 12 showing a further embodiment of the invention. This embodiment is particularly suitable for assaying genomic DNA but is also suitable for assaying the presence of another double-stranded oligonucleotide, such as a double-stranded RNA. In this embodiment, the method proceeds in two stages: a detection stage and a amplification stage. Furthermore, this embodiment is based on the simultaneous separate assaying of both the coding X strand and the non-coding strand of the assayed sequence in two separate vessels. Thus, there are in fact two detection systems, one 1204 for the coding strand and the other 1204' for the non-coding strand. Detection system 1204 comprises a first DNA molecule 1220 comprising a functional promoter P⁺ followed by the sequences $D_1$ and A, the latter being complementary to the sequence A' of the assayed DNA sequence. Second DNA molecule comprises sequence B, complementary to sequence B' of the assayed DNA sequence followed by the sequence $D_2'$ and the sequence P', which is the sequence of the non-template strand of a promoter. Upon hybridization and transcription, the oligonucleotide 1210 is produced having the sequences $D_1'$, $A_1'$, $B_1$, $D_2$ and P, the latter being the template strand of a promoter.

The detection system 1204' comprises a first DNA molecule 1220' having the sequence P' followed by a sequence D1' and A' and the second DNA molecule 1222' comprises the sequences B', $D_2$ and a functional promoter P⁺. Upon hybridization with the non-coding strand of the assayed DNA sequence 1202', transcription, an oligonucleotide 1210' is produced having the sequences P, $D_1$, A, B and $D_2$. The transcription conditions in at least one of the two detection systems are such whereby oligonucleotide 1210 and/or 1210' is a DNA/RNA hybrid.

$D_1$, and $D_2$ sequence are DIS, similar as in the embodiment of FIG. 10.

At the next stage, oligonucleotides 1210 and 1210' are mixed with one another and together with oligonucleotide 1284 consisting of the sequence P' and upon hybridization, double-stranded oligonucleotide construct 1286 is obtained which has two functional promoters P⁺ which induce transcription in opposite directions. Upon transcription, oligonucleotides 1288 and 1290 are produced which are in fact identical to 1210 and 1210', respectively, and the reaction proceeds in itself as an amplifying manner.

One of the advantages of the assaying system according to this embodiment is in that the incorporation of an "n+1" nucleotide into the transcribed nucleotide is of no effect.

In all embodiments described herein, the readouts of the amplification of the produced oligonucleotide, indicating the presence of the assayed DNA in the sample, can be performed in a number of ways. One such method is spectromotic measurement of absorption of nucleic acids. Spectrophotometry is a known-method for quantifying nucleic acids. As the amplification reaction will result in synthesis of a mixed RNA/DNA oligonucleotide, which causes an increase in optical density, this will facilitate spectrophotometrical quantification.

In those embodiments wherein double-stranded oligonucleotide are produced, such as the case is in the embodiments of FIGS. 10–12, the readout may be based on the detection of such double-stranded constructs.

Another method of detection, is that involving the use of a Read Out (RO) sequence, used in the embodiment of FIG. 11 and which can also be used in other embodiments, e.g. that of FIG. 12 (attached to the 5' end of the P sequence). Such an RO sequence may be a stretch made out of iso-nucleotides and if labelled iso-nucleotide are included in the reaction medium, such will be incorporated only in that or in the complementary RO' sequence; appearance of a labeling in an oligonucleotide will thus be an indication of the presence of the assayed sequence in the sample.

As will be appreciated, there are many other possible readout systems.

We claim:

1. A method for detecting the presence of an assayed nucleic acid sequence in a sample, comprising the steps of:
   (a) incubating the sample within a detection system comprising:
      (i) a first oligonucleotide having a double-stranded promoter sequence and a 5' end sequence which is complementary to the 5' end portion of the assayed nucleic acid sequence;
      (ii) a second oligonucleotide having a single-stranded 3' end sequence being complementary to a 3' end portion of the assayed nucleic acid sequence, and further having a sequence which can be transcribed into a triggering oligonucleotide capable of initiating a reaction in a transcription system in which a transcription product is produced; the 3' end sequence of the second oligonucleotide and the 5' end sequence of the first oligonucleotide are either complementary together to the entire assayed nucleic acid sequence or to only part thereof, thus leaving an intermediate portion in the assayed nucleic acid sequence having no complementary counterpart in either the first or the second oligonucleotide, in which latter case the detection ensemble further comprises
      (iii) a third oligonucleotide being complementary to said intermediate portion;
   said first, second and third oligonucleotides, being either DNA oligonucleotides, a DNA oligonucleotide comprising RNA nucleotides (rNTPs), or a DNA oligonucleotide comprising analogs of DNA nucleotides (dNTPs) or of rNTPs;
   (b) providing conditions allowing hybridization of said first oligonucleotide and said second oligonucleotide, and where present also said third oligonucleotide, with said assayed nucleic acid sequence, and optionally providing also a ligase to allow ligation of adjacent ends of said first, second and third oligonucleotides;
   (c) providing conditions allowing the production of said triggering oligonucleotide, said conditions comprising the provision of:
      (i) an RNA polymerase;
      (ii) 4 species of nucleotides, of which at least two are rNTPs and of the remaining two
         at least one is a non-rNTP being a dNTP or a nucleotide analog other than rNTP or dNTP, or
         at least one is a combination of rNTP and said non-rNTP of the same nucleotide species, the said non-rNTP being in abundance over said rNTP; and
      (iii) conditions allowing the incorporation of rNTPs into the triggering oligonucleotide produced by the RNA polymerase;
   (d) contacting the triggering oligonucleotide with an amplification system in which the triggering oligonucleotide induces formation of reporter oligonucleotides; and
   (e) detecting the presence of said reporter oligonucleotide, positive results indicating the presence of said assayed nucleic acid sequence, in said sample.

2. A method according to claim 1, wherein after step (b) the temperature is transiently raised to a point in which only essentially perfectly matched hybrids formed in step (b) remain hybridized while all other hybrids in which the individual strands do not perfectly match to one another are melted.

3. A method according to claim 2, wherein after raising the temperature, blocker oligonucleotide molecules are added which are complementary to a sequence in said first or said second oligonucleotide whereby said blocker molecules compete with the assayed nucleic acid sequence in hybridization to the first or the second oligonucleotides, hybridization of the blocker molecule to either the first or second oligonucleotide blocks, rehybridization of the assayed nucleic acid sequence to the first or the second oligonucleotide.

4. A method according to claim 1, wherein said promoter is double-stranded in at least a portion thereof which is essential for its transcription promoting activity.

5. A method according to claim 1, wherein said promoter is single-stranded in at least a portion thereof which is essential for its transcription promoting activity and during or after step (b) a sequence which is complementary to said at least one portion of the promoter is added, rendering the promoter functional.

6. A method according to claim 5, wherein prior to addition of the sequence complementary to the single-stranded portion of the promoter, blocker oligonucleotide molecules are added which hybridize to free first oligonucleotides so as to avoid subsequent hybridization of the sequences complementary to the single-stranded portion of the promoter to said free first oligonucleotides, said blocker molecule being incapable of hybridizing to said first oligonucleotides which have already hybridized to the assayed nucleic acid sequence.

7. A method according to claim 1, wherein said second oligonucleotides are bound to a solid support and following step (b) there is a washing step intended for removal of oligonucleotide molecules which are unbound to the solid support.

8. A method according to claim 1, wherein:
the amplification system comprises: a fourth oligonucleotide molecule comprising a promoter which is single-stranded in at least a portion thereof which is essential for its transcription promoting activity and is thus inactive, and further comprises a reporter oligonucleotide sequence;
the triggering oligonucleotide being complementary to said single-stranded part of the promoter of the fourth oligonucleotide molecule and upon hybridization thereof to the single-stranded part of the promoter, the promoter becomes functional and in the presence of transcription reagents, a reporter oligonucleotide, being a transcript of the fourth oligonucleotide, is produced.

9. A method according to claim 8, wherein the transcript comprises the triggering oligonucleotide.

10. A method according to claim 1, wherein:
the amplification system comprises a fifth oligonucleotide and a sixth oligonucleotide; the fifth oligonucleotide comprises a functional promoter and at its 5' end, and a single-stranded sequence which is complementary to the 5' end portion of the triggering oligonucleotide; the sixth oligonucleotide comprising at its 3' end, a single-stranded sequence which is complementary to the remaining 3' end portion of the triggering oligonucleotide, and also comprise at it 5' end a sequence which is capable of being transcribed to said reporter oligonucleotide sequence;
the triggering oligonucleotide comprises a sequence complementary to the single-stranded portions of said fifth and said sixth oligonucleotides whereby, when the triggering oligonucleotide is contacted with the fifth and sixth oligonucleotides, the three molecules hybridize to form an oligonucleotide heteroduplex, whereupon in the presence of transcription reagents, an oligonucleotide transcript that comprises the reporting oligonucleotide is transcribed.

11. A method according to claim 10, wherein said oligonucleotide transcript comprises the triggering oligonucleotide.

12. A method according to claim 1, wherein:
the amplification system comprises a seventh oligonucleotide and an eighth oligonucleotide both having functional, double-stranded promoters; the seventh oligonucleotide has an antisense sequence attached to the non-template strand of the promoter which is complementary to the 3' end sequence of the triggering oligonucleotide; the eighth oligonucleotide has an antisense sequence attached to the non-template strand of the promoter which is identical to the 5' end sequence of the triggering oligonucleotide; and
step (d) comprises:
i contacting the triggering oligonucleotide with said amplification system, and providing conditions allowing the hybridization of the triggering oligonucleotide to the antisense sequence in the seventh oligonucleotide; optionally ligating the triggering oligonucleotide to the seventh oligonucleotide;
ii providing conditions for oligonucleotide transcription, in which a first amplification transcript is produced, with the triggering oligonucleotide serving as a template;
iii maintaining or providing conditions allowing hybridization of said first amplification transcript to the antisense sequence in said eighth oligonucleotide; and
iv providing or maintaining conditions for oligonucleotide transcription so that a second amplification transcript is produced, which is identical to the triggering oligonucleotide;
whereby under said conditions there is a cross triggering of oligonucleotide transcription by hybridization of said first and said second amplification transcripts to said eighth and seventh oligonucleotides, respectively, the detecting of the presence of the amplification transcripts being an indication of the presence of said assayed nucleic acid sequence in the sample.

13. A method for detecting the presence of an assayed nucleic acid sequence in a sample, comprising the step of:
(a) reacting the sample with a detection system comprising:
a single-stranded first oligonucleotide having from its 3' to its 5' end three sequence portions linked to one another comprising a first arbitrary portion, a second arbitrary portion of 1–5 bases long, and a 5' end sequence which is complementary to the 5' end portion of the assayed nucleic acid sequence;
a second oligonucleotide comprising a single-stranded 3' end sequence being complementary to a 3' end portion of the assayed nucleic acid sequence, and further comprising a third double-stranded arbitrary portion;
(b) incubating under conditions to allow hybridization of the assayed nucleic acid sequence to said first single-stranded oligonucleotide and to said second oligonucleotide to produce oligonucleotide hybrids;

(c) raising the temperature to a point in which only essentially perfectly matched hybrids formed in step (b) remain hybridized while all other hybrids in which the individual strands do not perfectly match to one another are melted;

(d) adding a blocker oligonucleotide molecule, being a single-stranded oligonucleotide comprising at its 5' end a sequence complementary to said second arbitrary portion and a sequence, at its 3' end complementary to the 5' end portion of the assayed nucleic acid sequence and providing conditions allowing hybridization of said blocker molecule with free said first single-stranded oligonucleotide; adding a promoter DNA molecule, comprising a double-stranded functional promoter and a sequence complementary to the first and second arbitrary portions attached to a non-template strand and providing conditions for hybridization, whereby a hybrid comprising the assayed nucleic acid sequence, said promoter oligonucleotide molecule, said first single-stranded oligonucleotide and said second oligonucleotide is obtained from which an oligonucleotide transcript can be transcribed;

(e) adding transcription reagents and incubating under conditions to allow the formation of oligonucleotide transcripts having a triggering oligonucleotide;

(f) contacting the oligonucleotide transcripts with an amplification system in which the triggering oligonucleotide sequence induces formation of oligonucleotide molecules containing the reporter nucleotide sequence; and (g) detecting the presence of said reporter oligonucleotide sequence, positive results indicating the presence of said assayed oligonucleotide sequence in said sample.

14. A method according to claim 13, wherein the conditions for hybridization in step (d), comprises lowering of temperature.

15. A method according to claim 1, wherein the detection of the presence of said assayed nucleic acid in the sample comprise the detection of a specific oligonucleotide sequence.

16. A method according to claim 1 or 13, wherein the presence of the assayed nucleic acid sequence in the sample is based on the detection of an accumulation of oligonucleotide transcripts following the addition of transcription reagents.

17. A method according to claim 16, wherein the accumulation of oligonucleotide transcripts is detected by light absorbance.

18. A method according to claim 1, wherein:
the first oligonucleotide comprises:
a functional promoter followed by a single stranded C nucleotide;
the second oligonucleotide comprises a terminal G-A-T triplet
and wherein step c(ii) comprises providing G-A-T triplets in abundance over the G nucleotide.

19. A method according to claim 18, wherein:
the amplification system comprises a ninth and tenth oligonucleotide molecules both having promoters which are, a priori, not functional due to a lack of either a TA or UA doublet at the 5' end of the template strand, the ninth oligonucleotide molecule comprising an antisense sequence attached to the non-template strand of the promoter which is complementary to the 3' sequence of the triggering oligonucleotide, the tenth oligonucleotide molecule has an antisense sequence attached to the non-template strand of the promoter which is identical to the 5' end sequence of the triggering oligonucleotide, the method further comprising in step (d):
i contacting the triggering oligonucleotide with said amplification system and providing conditions allowing the hybridization of the triggering oligonucleotide to the antisense sequence in the ninth oligonucleotide; optionally ligating the triggering oligonucleotide to the ninth oligonucleotide molecule;

ii providing conditions for oligonucleotide transcription and providing a TAG nucleotide triplet in the transcription system, whereby a third amplification transcript is produced having a TAG triplet at its 5' end;

iii maintaining or providing conditions allowing hybridization of said third amplification transcript to the antisense sequence in said tenth oligonucleotide; optionally ligating the third amplification transcript to the tenth molecule;

iv providing conditions for oligonucleotide transcription and providing a TAG nucleotide triplet in the transcription system in which a second oligonucleotide is produced which is identical to the triggering oligonucleotide, whereby under said conditions there is a cross-triggering of oligonucleotide transcription by hybridization of said first and said second oligonucleotide transcripts to said ninth and said tenth oligonucleotides, respectively; the detection of the presence of the amplification transcripts being an indication of the presence of said assayed nucleic acid sequence in the sample.

20. A method according to claim 1, wherein the assayed nucleic acid sequence is double-stranded and wherein:
the second oligonucleotide each comprising a sequence at its terminal which is transcribed to one strand of a promoter, wherein the method further comprises:
(a) melting the assayed nucleic acid sequence to single strands;
(b) detecting each separate strand as defined in step (a) of claim 1;
(c) mixing the triggering oligonucleotide products of the two detection systems of step (b) together and adding a single-stranded promoter sequence capable of completing the promoter of each of the triggering oligonucleotides produced to a double-stranded functional promoter;
(d) providing conditions allowing production of oligonucleotide transcripts; and
(e) detecting the presence of said transcripts, positive result indicating the presence of said assayed nucleic acid sequence in said sample.

* * * * *